United States Patent [19]
Nugent et al.

[11] Patent Number: 5,981,537
[45] Date of Patent: Nov. 9, 1999

[54] PYRIMIDINE-THIOALKYL AND ALKYLETHER COMPOUNDS

[75] Inventors: Richard A. Nugent, Galesburg; Stephen T. Schlachter, Kalamazoo; Michael J. Murphy, Kalamazoo; Joel Morris, Kalamazoo; Richard C. Thomas, Kalamazoo; Donn G. Wishka, Kalamazoo; Fritz Reusser, Portage; Gary J. Cleek, Kalamazoo; Irene W. Althaus, Portage, all of Mich.

[73] Assignee: Pharmacia & Upjohn Company, Kalamazoo, Mich.

[21] Appl. No.: 08/640,898

[22] PCT Filed: Nov. 9, 1994

[86] PCT No.: PCT/US94/12713

§ 371 Date: May 9, 1996

§ 102(e) Date: May 9, 1996

[87] PCT Pub. No.: WO95/13267

PCT Pub. Date: May 18, 1995

Related U.S. Application Data

[63] Continuation-in-part of application No. 08/152,449, Nov. 12, 1993, abandoned.

[51] Int. Cl.$^6$ ...................... A61K 31/505; A61K 31/535; C07D 413/00; C07D 239/02

[52] U.S. Cl. .................. 514/274; 514/227.8; 514/232.2; 514/235.8; 514/249; 514/255; 544/60; 544/120; 544/121; 544/122; 544/123; 544/295; 544/296; 544/315; 544/316; 544/317; 544/318

[58] Field of Search .............................. 544/60, 120, 121, 544/122, 123, 295, 296, 315, 316, 317, 318; 514/227.8, 232.2, 235.8, 274

[56] References Cited

U.S. PATENT DOCUMENTS

| | | | |
|---|---|---|---|
| 4,724,232 | 2/1988 | Rideout et al. | 514/50 |
| 4,933,348 | 6/1990 | Mase et al. | 514/274 |
| 5,025,016 | 6/1991 | Abreas et al. | 514/274 |
| 5,616,739 | 4/1997 | Mas et al. | 549/510 |
| 5,621,121 | 4/1997 | Commercon et al. | 549/510 |

FOREIGN PATENT DOCUMENTS

| | | | |
|---|---|---|---|
| 124 630 | 5/1983 | European Pat. Off. . | |
| 0 191 443 | 8/1986 | European Pat. Off. . | |
| 477 778 | 4/1992 | European Pat. Off. . | |
| 567 107 | 10/1993 | European Pat. Off. . | |
| 0 663 905 B1 | 1/1997 | European Pat. Off. | C07D 305/14 |
| 1 216 220 | 4/1960 | France . | |
| 40 29 648 | 3/1992 | Germany . | |
| 744 867 | 9/1953 | United Kingdom . | |

OTHER PUBLICATIONS

Wempen et al., Pyrimidines. I. The Synthesis of 6–Fluorocytosine and Related Compounds, Journal of Medicinal Chemistry, vol. 6, No. 6, pp. 688–693, Nov. 1963.

Gueritte–Voegelein, Francoise; Guenard, Daniel; Lavelle, Francois; Le Goff, Marie–Therese; Mangatal, Lydie; Potier, Pierre; Relationships between the Structure of Taxol Analogues and Their Antimitotic Activity, J. Med. Chem. 1991, 34, 992–998.

Caplus An=1967:85747; Nagpal et al., 4.beta.–Chloroethylaminopyrimidines And The Formation Of Imidazolidinol [1,2–c]pyrimidines On Acid Treatment Of 4–bis(.beta.–hydroxymethylamino)pyrimidines, Tetrahedron, vol. 23, Issue 3, pp. 1294–1304.

Schickaneder, H., Engler, H., Szelenyi, 2–[*3–Pyridinylmethyl)thio*]*pyrimidine Derivatives: New Bronchosecretolytic Agents*, J. Med. Chem. 1987, 300, 547–551.

Baker, B.R., Joseph J.P., Williams, J.H., *Puromycin, Synthetic Studies, VI. Analogs of 6–Dimethylaminopurine*, J. Org. Chem., 1954, 19, 1793–1801.

Norman, Colin, *$2–Billion Program Urged for AIDS*, Science, 661–662 (1986).

Curran, JW, Morgan, WM, Hardy, AM, Jaffe, HW, Darrow, WW, Dowdle, WR, *The Epidemiology of AIDS: Current Status and Future Prospecs,* Science, vol. 229, 1352–1357).

Pauwerls, R, Andries, K, Desmyer, J, Schols, D, Kukla, MJ, Breslin, HJ, Raeymaeckers, A, VanGelder, J, Woestenborghs, R, Heykans, J, Schellekens, K, Janssen, MAC, DeClereq, E, Janssen, PAJ, *Potent and selective inhibition of HIV–1 replication in vitro by a novel series of TIBO derivatives,* Nature, vol. 343, 470–474, Feb. 1, 1990.

Koppel, HC, Springer, RH, Robins, RK, Cheng, CC, *Pryimidines. V. Analogs of 2–(o–Chlorobenzylthio)–4–dimethylamino–5–methylpyrimidine* (Bayer DG–428), J. Org. Chem. Jan. 1962, 27, 181–185.

(List continued on next page.)

*Primary Examiner*—Richard L. Raymond
*Assistant Examiner*—Brenda Coleman
*Attorney, Agent, or Firm*—William G. Jameson

[57] ABSTRACT

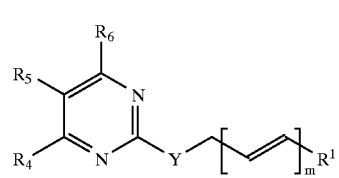

(I)

The subject invention relates to pyrimidine-thioalkyl and alkylether compounds of Formula (I) and pyrimidine-thioalkyl and alkylethers of Formula (IA), namely the compounds of Formula (I) where $R^4$ is selected from the group consisting of —H or —$NR_{15}R_{16}$ where $R_{15}$ is —H and $R_{16}$ is —H, $C_1$–$C_6$ alkyl, —$NH_2$ or $R_{15}$ and $R_{16}$ taken together with the —N form 1-pyrrolidino, 1-morpholino or 1-piperidino; and $R_6$ is selected from the group consisting of —H, or halo (preferably —Cl); with the overall proviso that $R_4$ and $R_6$ are not both —H. The compounds of Formula (IA) are useful in the treatment of individuals who are HIV positive.

20 Claims, No Drawings

OTHER PUBLICATIONS

Ward, AD, Baker, BR, *Irreversible Enzyme Inhibitors, 200. Active–site–direced Inhibitors of Deoxycytidine Kinase,* Journal of Medicinal Chemistry, 1977, vol. 20, No. 1, 88–92.

Budesinsky, Z, Bruna, L, Svab, A, Capek, A, *5–(3–Iodopropargyloxy)pyrimidines as effective fungistatics,* Collect. Czech. Chem. Commun. 1975, 40(4), 1078–88 (CA 83:114326e).

Kropf, H, Mirzai Amirabadi, H, *4–t–Butylperoxypyrimidine, 2,4–Di–t–butylperoxy–und 4,6–Di–t–butylperoxypyrimidine,* Synthesis, May 1981, 397–400.

Koppel, HC, Springer, RH, Cheng, CC, *Pyrimidines. IV. Aziridinylpyrimidines,* J. Org. Chem. 1961, vol. 26, 1884–1890.

Tjarks, W, Gabel, D, *Boron–containing Thiouracil Derivatives for Neutron–capture Therapy of melanoma,* Med. Chem., 1991, 34, 315–319.

Larder, B, Purifoy, D, Powell, K, Darby, G, *AIDS virus reverse transcriptase defined by high level expression in Escherichia coli,* The EMBO Journal, vol. 6, No. 10, pp. 3133–3137, 1987.

*Cloned Viral Protein Vaccine for Foot–and–Mouth Disease: Responses in Cattle and Swine,* Science, vol. 214, Dec. 4, 1981, 1125–1129.

Nara, PL, Fischinger, PJ, *Quantitative infectivity assay for HIV–1 and –2,* Nature, vol. 332, Mar. 31, 1998, 469–470.

Busso, M, Mian, AM, Hahn, EF, Resnick, L., *Nucleotide Dimers Suppress HIV Expression In Vitro,* AIDS Research and Human Retroviruses, vol. 4, No. 6, 1988, 449–455.

Merluzzi, VJ, Hargrave, KD, Labadia, M, Grozinger, K, Skoog, M, Wu, JC, Shih, C, Eckner, K, Hatox, S, Adams, J, Rosenthal, AS, Faanes, R, Eckner, RJ, Koup, RA, Sullivan, JL, *Inhibition of HIV–1 Replication by a Nonnucleoside Reverse Transcripase Inhibitor,* Science, Dec. 7, 1990, 1411–1413.

PYRIMIDINE-THIOALKYL AND ALKYLETHER COMPOUNDS

This application is the National Phase of PCT/US94/12713, filed Nov. 9, 1994 which is a continuation-in-part of application Ser. No. 08/152,449, filed Nov. 12, 1993 now abandoned.

BACKGROUND OF THE INVENTION

1. Field of Invention

The pyrimidine-thioalkyl and alkylether derivatives of Formula IA are useful in the treatment of individuals who are HIV positive, whether or not they show AIDS symptoms at the present time. The pyrimidine-thioalkyl and alkylether derivatives of Formula IB are useful in the preparation of the pyrimidine-thioalkyl and alkylether derivatives of Formula IA.

2. Description of the Related Art

U.S. Pat. No. 5,025,016 (and EP 124 630) pyrimidine-thioalkyl pyridine derivatives corresponding to the general formula

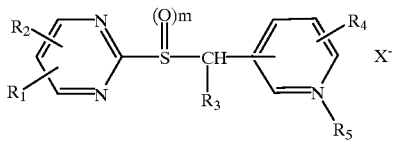

in which $R_1$ to $R_4$, independently of one another, represent hydrogen, lower alkyl, halogen, amino or hydroxy groups, $R_5$ represents a free electron pair or a lower alkyl group, a halogen atom, m has the value 0 or 1, the pyrimidine-thioalkyl group being bonded in the 2-, 3- or 4- position of the pyridine ring, and to therapeutically compatible acid addition salts thereof. The compounds allegedly exhibit surprisingly improved bronchosecretolytic and myucolytic activity as well as having been found to show antiphlogistic activity.

J. Med Chem. 1987, 30, 547–551 describes various 2-[(pyridinylmethyl)thio]-pyrimidine derivatives and the influence thereof on bronchosecretolytic properties in the phenol red screening model of the mouse in comparison to the known drug ambroxol.

EP 477 778 (Derwent 92-106190/14) describes various benzene, pyridine and pyrimidine derivatives as ACAT enzyme inhibitors, for treating arteriosclerosis, and cerebrovascular disease.

J. Org. Chem, 1954, 19, 1793–1801 describes pyrimidine derivatives, including
2-benzylmercapto-4-amino-6-pyrimidinol,
   2-benzylmercapto-4-amino-6-chloropyrimidine,
2-benzylmercapto-4-amino-6-diethylaminopyrimnidine as well as analogs of 6-dimethylaminopurine.

British Patent 744,867 (CA 51:2063i) describes various 2-R'-S-6-RR'N-substituted 4-aminopyrimidines.

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousand people will develop AIDS in the next five years, see Science, 1352–1357 (1985). On Mar. 20, 1987, the FDA approved the use of the compound, AZT (zidovudine), to treat AIDS patients with a recent initial episode of pneumocystis carinii pneumonia, AIDS patients with conditions other than pneumocystis carinii pneumonia or patients infected with the virus with an absolute CD4 lymphocyte count of less than $200/mm^3$ in the peripheral blood. AZT is a known inhibitor of viral reverse transcriptase, an enzyme necessary for human immunodeficiency virus replication.

U.S. Patent 4,724,232 claims a method of treating humans having acquired immunodeficiency syndrome utilizing 3'-azido-3'-deoxy-thymidine (azidothymidine, AZT).

It is known in the art that certain antibiotics and polyanionic dyes inhibit retrovirus reverse transcriptase.

Many publications have reported the ability of various sulfated compounds to inhibit virus replication, including HIV.

Nature 343, 470 (1990) and Science 250, 1411 (1990) disclose potent benzodiazepin type reverse transcriptase inhibitors. The compounds of the present invention are not benzodiazepin type compounds.

J. Org. Chem. 1962, 27, 181–185 describes various 2-benzylthio pyrimidine derivatives, including 4chloro-5-methyl-2-[(phenylmethyl)thio]-pyrimidine, 4-chloro-5-methyl-2-[[(2,4-dichloro-phenyl)methyl]thio]-pyrimidine, 4-chloro-5-methyl-2-[[(2-chloro-phenyl)methyl]thio]-pyrimidine, and 4-chloro-5-methyl-2-[[(4-chloro-phenyl)methyl]thio]-pyrimidine and their activity as antitumor compounds in screens against SA-180, CA 755, and L-1210 tumor systems.

J. Med. Chem. 1977, 20, 88–92 describes 2-alkoxy and 2-alkylthio-4amino pyrimdines, including 2-[(phenylmethyl)thio]4-pyrimidinamine, 2-[[(4-chlorophenyl)methyl]thio]-4-pyrimidinamine, 2-[(3-pyridinylmethyl)thio]4pyrimidinamine, and 2-(phenylmethoxy)-4-pyrimidinamine, and their activity as inhibitors of deoxycytidine kinase.

Collect. Czech. Chem. Comm. 1975, 40, 1078–1088 (CA 83: 114326e) describes 5-(3-iodopropargyloxy)pyrimidines as effective fungistatics.

Synthesis 1981, 397–400 describes peroxypyrimidines

J. Org. Chem. 1961, 26, 1884 describes the synthesis of aziridinyl pyrimidines as analogs of methioprim.

J. Med. Chem. 1991, 34, 315–319 describes derivataives of thiouracil which have dihydroxyboryl group at the C-5 position. These compounds are useful for B neutron-capture therapy of malignant melanoma.

SUMMARY OF INVENTION

Disclosed are pyrimidine-thioalkyl and alkylether compounds of Formula I

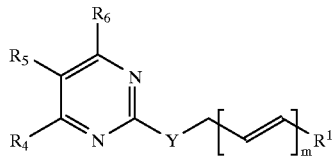

and therapeutically/pharmaceutically compatible acid addition salts thereof.

The compounds corresponding to Formula I may exist in various tautomeric formulas, and are included within the scope of Formula I as well as Formula IA and IB.

DETAILED DESCRIPTION OF THE INVENTION

Disclosed are pyrimidine-thioalkyl and alkylether compounds of Formula I

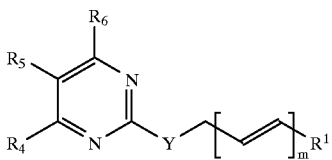

where
m is 0 or 1;
$R^1$ is selected from the group consisting of —C≡CH,

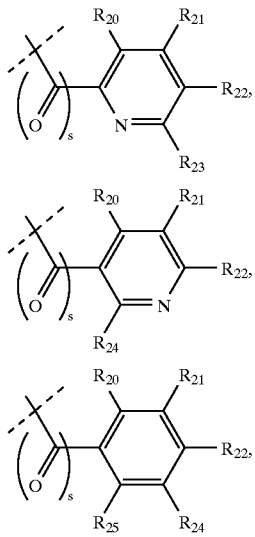

where s is 0 or 1 (preferably 0) and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, —halo, —OH, —CN, phenyl, phenylthio, —styryl, —$CO_2(R_{31})$, —$CON(R_{31})(R_{32})$, —$CO(R_{31})$, —$(CH_2)_n$—$N(R_{31})(R_{32})$, —$C(OH)(R_{31})(R_{33})$, —$(CH_2)_nN(R_{31})(CO(R_{33}))$, —$(CH_2)_nN(R_{31})(SO_2(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with -H, $C_1$–$C_6$ alkyl, $C_1$–$C_6$ alkoxy, —OH, —$CH_2OH$, or —$(CH_2)_n$—$N(R_{31})(R_{32})$ and the saturated ring may be optionally substituted with —H, —$C_1$–$C_6$ alkyl, —$C_1$–$C_6$ alkoxy, —OH, —$CH_2OH$, —$(CH_2)_n$—$N(R_{31})(R_{32})$ or oxo (=O);
where n is 0–3 and $R_{31}$, $R_{32}$, and $R_{33}$ are the same or different and are selected from
—H,
$C_1$–$C_6$ alkyl,
phenyl optionally substituted with 1, 2, or 3-halo, $C_1$–$C_6$ alkyl, $_1$–$C_6$ alkoxy, —$CF_3$, —$NO_2$, —OH, —CN),
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl,
or a member selected from the group consisting of:
1-cyclohexenyl, 2-pyrimidinyl, 4-pyrimnidinyl, 5-pyrimidinyl, 2-imidazolyl, 4-imidazolyl, 2-benzothiazolyl, 2-benzoxazolyl, 2-benzimidazolyl, 2-oxazolyl, 4oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl;
and with the overall provisio that $R_1$ is not 2-pyrazinyl; $R_{20}$, $R_{21}$, $R_{22}$, $R_{23}$, $R_{24}$, $R_{25}$ are not $CO_2H$;
Y is selected from —S—, —S(O)—, —$S(O)_2$, or —O—;
$R_4$ is selected from the group consisting of —H, —OH, halo or —$NR_{15}R_{16}$ where $R_{15}$ is —H and $R_{16}$ is —H, $C_{1-6}$ alkyl, —$NH_2$ or $R_{15}$ and $R_{16}$ taken together with the —N form 1-pyrrolidino, 1-morpholino or 1-piperidino;
$R_5$ is selected from the group consisting of —H, halo, cyclohexyl, $C_{1-4}$ alkyl or $C_{1-3}$ alkoxy; and
$R_6$ is selected from the group consisting of —H, —OH or halo (preferably —Cl), with the overall provisio that $R_4$ and $R_6$ are not both —H; and
pharmaceutically acceptable salts, hydrates, N-oxides and solvates thereof.

An embodiment of the present invention are pyrimidine-thioalkyl and alklyether anti-AIDS compounds of Formula IA, namely the compounds of Formula I where
$R_4$ is selected from the group consisting of —H or —$NR_{15}R_{16}$ where $R_{15}$ is —H and $R_{16}$ is —H, $C_1$–$C_6$ alkyl, —$NH_2$ or $R_{15}$ and $R_{16}$ taken together with the -N form 1-pyrrolidino, 1-morpholino or 1-piperidino; and
$R_6$ is selected from the group consisting of —H or halo (preferably —Cl).
Compounds of Formula IB, namely the compounds of Formula I where:
i) $R_4$ and/or $R_6$ are —OH; or
ii) $R_4$ and $R_6$ are both halo,
are useful as intermediates to produce the pyrimidine-thioalkyl and alkylether anti-AIDS compounds of Formula IA.

An embodiment of the present invention are compounds of Formula I (as well as Formula IA and IB) where Y is —O—.

A preferred embodiment of the present invention are compounds of Formula I (as well as Formula IA and IB) where s is 0 and Y is selected from the group consisting of —S—, —S(O)—or —$S(O)_2$; more preferably Y is —S—.
$R_4$ is preferably —$NH_2$.
m is preferably 0.
$R_6$ is preferably halo, more preferably —Cl.
$R^1$ is preferably selected from the group consisting of phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; 2-pyridyl (optionally substituted with —H, $C_1C_{-6}$ alkyl, $C_1$–$C_6$ alkoxy, —OH, —$CH_2OH$, or —$(CH_2)_n$—$N(R_{31})(R_{32})$; 1-naphthyl; or 2-naphthyl.

Novel pyrimidine-thioalkyl and alkylether anti-AIDS compounds of Formula IA include compounds where
$R_4$ is selected from the group consisting of —H or —$NR_{15}R_{16}$ where $R_{15}$ is —H and $R_{16}$ is —H, —$NH_2$ or R₁₅ and R₁₆ taken together with the —N form 1-pyrrolidino, 1-morpholino or 1-piperidino; and R$^1$ is selected from the group consisting of phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; naphthyl optionally substituted with one or 2 $C_1$–$C_4$ alkyl, $C_1$–$C_3$ alkoxy, halo, trifluoromethyl, $C_2$–$C_6$ dialkylamino, $C_1$–$C_3$ alkylthio or nitro; —C≡CH; or a member selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4dihydro)-1 H-pyrano[4,3-c]pyridinyl, 7-(3,4-dihydro)-2H-pyrano[3,2-c]pyridinyl, 5-(3,4dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3-c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6–1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1 ,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3-dihydro)-1H-indolyl, 6-(2,3-dihydro)-1H-indolyl, 7-(2,3-dihydro)-1H-indolyl, 4-(1,3-dihydro)-1 H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl or a member selected from the group consisting of:

4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 2,3-dihydrobenzofuran-2-yl, 1-methylimidazol-2-yl, quinoxalin-2-yl, isoquinolin-3-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcylcohexen-1-yl, 4-dihydronaphth-2-yl; other than 4-amino-6-chloro-2-(benzylthio)-pyrimidine, 4-chloro-2-[(phenylmethyl)thio]-pyrimidine, 4-chloro-5-methoxy-2-[(phenylmethyl)thio]-pyrimidine, 4-chloro-5-bromo-2-[(phenylmethyl)thio]-pyrimidine, 4-chloro-5-methyl-2-[(phenylmethyl)thio]-pyrimidine, 4-chloro-5-methyl-2-[[(2,4-dichloro-phenyl)methyl]thio]-pyrimidine, 4-chloro-5-methyl-2-[[(2-chloro-phenyl)methyl]thio]-pyrimidine, 4-chloro-5-methyl-2-[[(4-chloro-phenyl)methyl]thio]-pyrimidine, 4-chloro-5-bromo-2-[[(4-chloro-phenyl)methyl]thio]-pyrimidine, 4-chloro-5-bromo-2-[[(2,4-dichloro-phenyl)methyl]thio]-pyrimidine, 4-chloro-5-bromo-2-[[(2-chloro-phenyl)methyl]thio]-pyrimidine, 2-[(phenylmethyl)thio]4-pyrimidinamine, 2-[[(4-chlorophenyl)methyl]thio]-4-pyrimidinamine and 2-(phenylmethoxy)-4pyrimidinamine.

Preferred novel pyrimidine-thioalkyl and alkylether anti-AIDS compounds of Formula IA include compounds where $R_4$ is selected from the group consisting of —H or —NR₁₅R₁₆ where R₁₅ is —H and R₁₆ is —H, —NH₂ or R₁₅ and R₁₆ taken together with the —N form 1-pyrrolidino, 1-morpholino or 1-piperidino; and $R^1$ is phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro; other than 4-amino-6-chloro-2-(benzylthio)-pyrimidine,
4-amino-6-hydroxy-2-(benzylthio)-pyrimidine,
4-chloro-2-[(phenylmethyl)thio]-pyrimidine,
4-chloro-5-methoxy-2-[(phenylmethyl)thio]-pyrimidine,
4-chloro-5-bromo-2-[(phenylmethyl)thio]-pyrimidine,
4-chloro-5-methyl-2-[(phenylmethyl)thio]-pyrimidine,
4-chloro-5-methyl-2-[[(2,4-dichloro-phenyl)methyl]thio]-pyrimidine,
4-chloro-5-methyl-2-[[(2-chloro-phenyl)methyl]thio]-pyrimidine,
4-chloro-5-methyl-2-[[(4-chloro-phenyl)methyl]thio]-pyrimidine,
4-chloro-5-bromo-2-[[(4-chloro-phenyl)methyl]thio]-pyrimidine,
4-chloro-5-bromo-2-[[(2,4-dichloro-phenyl)methyl]thio]-pyrimidine,
4-chloro-5-bromo-2-[[(2-chloro-phenyl)methyl]thio]-pyrimidine,
2-[(phenylmethyl)thio]4-pyrimidinamine,
2-[[(4-chlorophenyl)methyl]thio]-4-pyrimidinamine,
2-[(3-pyridinylmethyl)thio]4-pyrimidinamine and
2-(phenylmethyoxy)-4pyrimidinamine.

Preferred novel pyrimidine-thioalkyl and alkylether anti-AIDS compounds of Formula IA include compounds where $R_4$ is selected from the group consisting of —H or —$NR_{15}R_{16}$ where $R_{15}$ is —H and $R_{16}$ is —H, —$NH_2$ or $R_{15}$ and $R_{16}$ taken together with the —N form 1-pyrrolidino, 1-morpholino or 1-piperidino.

The pyrimidine-thioalkyl compounds of Formula I are generally and most often prepared by contacting a 2-mercaptopyrimidine with an appropriate halide.

The pyrimidine-thioalkyl and alkylether compounds of Formula I include the compounds of EXAMPLES 1–167. Preferred are the novel anti-AIDS compounds of EXAMPLES 36, 43, 59, 64, 114 and 132 as well as the intermediate compounds of EXAMPLES 4, 9–17, 26, 27, 32, 74, 76, 82 and 110. Preferred prior art compounds useful as anti-AIDS compounds are the compounds of EXAMPLES 55, and 71.

Compound 132 is a particularly preferred anti-AIDS compound of the subject invention.

The pyrimidine-thioalkyl and alkylether compounds of Formula I form acid addition salts, some of the variable substituents are acids and as such form base addition salts when reacted with bases of sufficient strength. The pharmaceutically acceptable salts include both inorganic and organic bases. The preferred pharmaceutically acceptable salts include salts of the following bases, for example, hydroxide, ammonia, tromethamine (THAM), 2-amino-2-(hydroxymethyl)-1,3-propanediol. Suitable cations include, for example, sodium, potassium, calcium and magnesium.

The pyrimidine-thioalkyl and alkylether anti-AIDS compounds of Formula IA are useful as inhibitors of viral reverse transcriptase, an enzyme necessary for human immunodeficiency virus replication and therefore would be useful in the treatment of such diseases as AIDS.

The term human retrovirus (HRV) indicates human immunodeficiency virus type I, or strains thereof apparent to one skilled in the art, which belong to the same viral families and which create similar physiological effects in humans as various human retroviruses.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis, (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than 200/$mm^3$ in the peripheral blood.

The compounds of Formula IA can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends on the particular compound of Formula IA used, the particular condition being treated, the severity of the condition being treated, the age, weight, general physical condition of the particular patient, other medication the individual may be taking as is well known to those skilled in the art and can be more accurately determined by measuring the blood level or concentration of the compounds of Formula IA in the patient's blood and/or the patient's response to the particular condition being treated.

Patients who are HIV positive but asymptomatic would typically be treated with lower oral doses (about 0.2 to about 100 mg/kg/day. ARC (AIDS-related complex) and AIDS patients would typically be treated with higher oral doses (about 1 to about 500 mg/kg/day).

The pyrimidine-thioalkyl and alkylether anti-AIDS compounds of Formula IA of this invention can be used in conjunction with other antiviral agents such as AZT, ddI, ddC, with non-nucleoside anti-AIDS agents such as those disclosed in International Publication No. WO91/09849, published Jul. 11, 1991, and International Publication No. WO93/01181, published Jan. 21, 1993, and with protease inhibitors.

The utility of the pyrimidine-thioalkyl and alkylether anti-AIDS compounds of Formula IA of this invention can be determined by their ability to inhibit viral reverse transcriptase, an enzyme essential for human immunodeficiency virus replication. This enzyme has characteristics which differentiate it from other known cellular polymerases and it is a unique enzyme which is not found in uninfected cells. Viral reverse transcriptase is found in extracts from bacterial clones prepared according to the procedure described in AIDS Virus Reverse Transcriptase defined by high level expression in Escherichia coli, EMBO J. 6: 3133–3137 (1987). P236L viral reverse transcriptase is obtained by PNAS 90: 4713–4717 (1993). Inhibition of this enzyme is determined in a cell free assay which measures the level of radioactive precursors incorporated into DNA. Extracts prepared according to the procedure of Science, 1125–1129 (1981) are incubated in a mixture of inhibitor, 20 mM dithiothreitol, 60 mM sodium chloride, 0.05% NP-40, 10 mM magnesium chloride, 50 mM Tris pH 8.3, 10 $\mu$M [$^{35}$S]-labeled deoxynuleoside-5'-triphosphate, 10 $\mu$g/ml RNA template (poly rC or poly rG) and 5 pg/ml DNA primer (oligo dG or oligo dT) for 30 minutes at 37° C. Incorporation of radio-labeled percursor is determined by spotting aliquots of the reaction mixture on DE81 paper, washing the papers to remove unincorporated percursor, drying and determining counts. The results ($IC_{50}$ means the concentration, in $\mu$M of drug, required to inhibit the reverse transcriptase activity (P236L) to the extent of 50%) of various assay(s) are combined and reported as % inhibition and/or $IC_{50}$ (calculated) in Table I.

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3-C(=Z_1)$H. Groups $R_i$ and $R_j$ would represent monovalent variable substituents if attached to the formula $CH_3-CH_2-C(R_i)(R_j)$H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3-O-CH_2-CH(R_i)-CH_3$ represents a 2-substituted-1-methoxypropane compound. In a similar fashion, the symbol "=" represents a double bond, e.g., $CH_2=C(R_i)-O-CH_3$, and the symbol "≡" represents a triple bond, e.g., $HC\equiv C-CH(R_i)-CH_2-CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4chloro-2-methylpyridine can be represented in linear fashion by $N^*=C(CH_3)-CH=CCl-CH=C^*H$ with the convention that the atoms marked with an asterisk (*) are bonded to each other resulting in the formation of a ring. Likewise, the cyclic molecular fragment, 4-(ethyl)-1-piperazinyl can be represented by $-N^*-(CH_2)_2-N(C_2H_5)-CH_2-C^*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, $-C(X_1)(X_2)-$ the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_1$ attached to a carbon atom as $-C(=R_i)-$ might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give $-C(\alpha\text{-}R_{i-j})(\beta\text{-}R_{i-k})-$. For example, when the bivalent variable $R_6$, $-C(=R_6)-$ is defined to consist of two monovalent variable substituents, the two monovalent variable substituents are $\alpha$-$R_{6-1}$:$\beta$-$R_{6-2}$, . . . $\alpha$-$R_{6-9}$:$\beta$-$R_{6-10}$, etc, giving $-C(\alpha\text{-}R_{6-1})(\beta\text{-}R_{6-2})-$, . . . $-C(\alpha\text{-}R_{6-9})(\beta\text{-}R_{6-10})-$, etc. Likewise, for the bivalent variable $R_{11}$, $-C(=R_{11})-$, two monovalent variable substituents are $\alpha$-$R_{11-1}$:$\beta$-$R_{11-2}$. For a ring substituent for which separate $\alpha$ and $\beta$ orientations do not exist (e.g., due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form $-CH_2-CH_2-O-CO$ . . . " means a lactone in which the carbonyl is bonded to $C_2$. However, when designated ". . . $R_j$ and $R_i$ are taken together to form $-CO-O-CH_2-CH_2-$the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3-(CH_2)_n-O-CO-$ where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

TLC refers to thin-layer chromatography.

Chromatography refers to medium pressure chromatography on silica gel.

THF refers to tetrahydrofuran.

Saline refers to an aqueous saturated sodium chloride solution.

NMR refers to nuclear (proton) magnetic resonance spectroscopy, chemical shifts are reported in ppm (δ) downfield from tetramethylsilane.

IR refers to infrared spectroscopy.

–φ refers to phenyl ($C_6H_5$).

MS refers to mass spectrometry expressed as m/e or mass/charge unit. [M+H]$^+$ refers to the positive ion of a parent plus a hydrogen atom. EI refers to electron impact. CI refers to chemical ionization. FAB refers to fast atom bombardment.

Ether refers to diethyl ether.

Halo refers to a halogen atom (—Cl, —Br, —F or —I).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pyridinyl refers to the pyridyl radical as defined by IUPAC nomenclature. For example, 2-pyridyl (pyridine ring substituted in the 2-position).

When solvent pairs are used, the ratios of solvents used are volume/volume (v/v).

HIV refers to HIV-1.

Treatment refers to inhibition of the HIV virus and will differ depending on the infected individual. For individuals who are HIV positive (infected) but who are asymptomatic, the pyrimidine-thioalkyl derivatives of Formula IA will delay, or prevent, the onset of symptoms. For individuals who are HIV positive, symptomatic and are pre-AIDS or ARC patients, the pyrimidine-thioalkyl derivatives of Formula IA will delay, or prevent, the onset of "full blown AIDS". For individuals who have "full blown AIDS", the pyrimidine-thioalkyl and alkylether derivatives of Formula IA will extend survival time of these individuals.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Preparation of 4-amino-6-hydroxy-2-(2,6-difluorophenylmethylthio)pyrimidine; (Cpd #1)

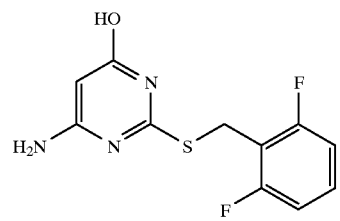

4-Amino-6-hydroxy-2-mercaptopyrimdine monohydrate (1.61 g, 10.0 mmol) is suspended in 50% ethanol (10 ml), then treated with solid sodium hydroxide (440 mg, 11.0 mmol) and stirred until the solid dissolved. 2,6-Difluorobenzyl bromide (2.17 g, 10.5 mmol) is added and the reaction heated to reflux for 1.5 hrs. After cooling to 22° C., the solid is collected, washed with water, then air dried. The title compound is recrystallized from ethanol, mp 245–246° C.

Following the general procedure of Example 1 and making noncritical changes, but using the appropriate halide, the following compounds are synthesized:

| | | mp (° C.) |
|---|---|---|
| Ex./Cpd #2 | 4-amino-2-(benzylthio)-6-hydroxypyrimidine | 236–239 |
| Ex./Cpd #3 | 4-amino-2-(2-methylphenylmethylthio)-6-hydroxypyrimidine | 250–251 |
| Ex./Cpd #4 | 4-amino-2-(3-methylphenylmethylthio)-6-hydroxypyrimidine | 230–231 |
| Ex./Cpd #5 | 4-amino-2-(4-methylphenylmethylthio)-6-hydroxypyrimidine | 266–267 |
| Ex./Cpd #6 | 4-amino-2-(3-trifluoromethylphenylmethylthio)-6-hydroxypyrimidine | 222–223 |
| Ex./Cpd #7 | 4-amino-2-(3-methoxyphenylmethylthio)-6-hydroxypyrimidine | 206–207 |
| Ex./Cpd #8 | 4-amino-2-(4-methoxyphenylmethylthio)-6-hydroxypyrimidine | 231–234 |
| Ex./Cpd #9 | 4-amino-2-(3-fluorophenylmethylthio)-6-hydroxypyrimidine | 92–93 |
| Ex./Cpd #10 | 4-amino-2-(3-chlorophenylmethylthio)-6-hydroxypyrimidine | 84–85 |
| Ex./Cpd #11 | 4-amino-2-(3-bromophenylmethylthio)-6-hydroxypyrimidine | 194–196 |
| Ex./Cpd #12 | 4-amino-2-(3-iodophenylmethylthio)-6-hydroxypyrimidine | 208–209 |
| Ex./Cpd #13 | 4-amino-2-(3-nitrophenylmethylthio)-6-hydroxypyrimidine | 263–264 |
| Ex./Cpd #14 | 4-amino-2-(3-carbomethoxyphenylmethylthio)-6-hydroxypyrimidine | |

-continued

| | | mp (° C.) |
|---|---|---|
| | NMR: (DMSO-$d_6$)8.01(s, 1H), 7.83(d, J=7.8, 1H), 7.74(d, J=7.8, 1H), 7.45 (t, J=7.8, 1H), 6.55(s, 2H), 4.95(s, 1H), 4.40(s, 2H), 3.84(s, 3H) | |
| Ex./Cpd #15 | 4-amino-2-(4-t-butylphenylmethylthio)-6-hydroxypyrimidine | 263–264 |
| Ex./Cpd #16 | 4-amino-2-(3,4-difluorophenylmethylthio)-6-hydroxypyrimidine | 222–224 |
| Ex./Cpd #17 | 4-amino-2-(3,4-dichlorophenylmethylthio)-6-hydroxypyrimidine | 255 |
| Ex./Cpd #18 | 4-amino-2-(3,5-dichlorophenylmethylthio)-6-hydroxypyrimidine | 276–277 |
| Ex./Cpd #19 | 4-amino-2-(2,4-dichlorophenylmethylthio)-6-hydroxypyrimidine | 278–279 |
| Ex./Cpd #20 | 4-amino-2-(3,5-dibromophenylmethylthio)-6-hydroxypyrimidine | 288–289 |
| Ex./Cpd #21 | 4-amino-5-cyclohexyl-2-(benzylthio)-6-hydroxypyrimidine | 195–196 |
| Ex./Cpd #22 | 4-amino-5-isopropyl-2-(benzylthio)-6-hydroxypyrimidine | 170–171 |
| Ex./Cpd #23 | 4-amino-2-(2-pyridylmethylthio)-6-hydroxypyrimidine | 219–220 |
| Ex./Cpd #24 | 4-amino-2-[2-(3-ethoxy)pyridylmethylthio]-6-hydroxypyrimidine | 214–216 |
| Ex./Cpd #25 | 4-amino-2-(3-pyridylmethylthio)-6-hydroxypyrimidine | 210–212 |
| Ex./Cpd #26 | 4-amino-2-(1-naphthylmethylthio)-6-hydroxypyrimidine | 240–242 |
| Ex./Cpd #27 | 4-amino-2-(2-naphthylmethylthio)-6-hydroxypyrimidine | 247–249 |
| Ex./Cpd #28 | 4-amino-2-(6,7-difluoro-2-naphthylmethylthio)-6-hydroxypyrimidine | 281–283(d) |
| Ex./Cpd #29 | 4-amino-2-(2-quinolinylmethylthio)-6-hydroxypyrimidine | |
| | NMR: (DMSO-$d_6$)8.33(d, J=8.4, 1H), 7.99(m, 2H), 7.76(dt, $J_d$=1.2, $J_t$=7.6, 1H), 7.68(d, J=8.4, 1H), 7.59(dt, $J_d$=1.2, $J_t$=7.6, 1H), 6.58(s, 2H), 4.97 (s, 1H), 4.63(s, 2H) | |
| Ex./Cpd #30 | 4-amino-2-(6-chloro-5-piperonylmethylthio)-6-hydroxypyrimidine | 254–255 |
| Ex./Cpd #32 | 4-amino-2-(E-styrylmethylthio)-6-hydroxypyrimidine | 253–254 |
| Ex./Cpd #33 | 4-amino-2-(propargylthio)-6-hydroxypyrimidine | 193–198 |

Example 34

Preparation of 4-amino-6-chloro-2-(2,6-difluorophenylmethylthio)-pyrimidine; (Cpd #34)

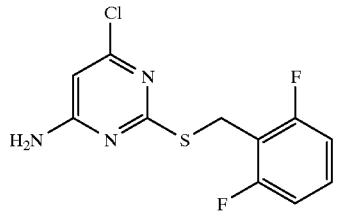

4-amino-6-hydroxy-2-(2,6-difluorophenylmethylthio) pyrimidine (1.33 g, 4.94 mmol; Cpd #1) and 2-picoline (0.5 ml) are heated in refluxing $POCl_3$ (6 ml) overnight. After removing excess solvent in vacuo, the residue is treated with ice, then refluxed for 30 min. The aqueous layer is decanted, then the residue treated with excess $NH_4OH$ and refluxed for 30 min. After cooling, the solid is collected and washed with water then recrystallized from toluene, mp 154° C.

Following the general procedure of Example 34 and making noncritical changes, but beginning with the appropriate hydroxy pyrimidine, the following compounds are synthesized:

| | | mp (° C.) |
|---|---|---|
| Ex./Cpd #34A | 4-amino-6-chloro-2-(benzylthio)-pyrimidine | 112–114.6 |
| Ex./Cpd #35 | 4-amino-6-chloro-2-(2-methylphenylmethylthio)-pyrimidine | 129–131 |
| Ex./Cpd #36 | 4-amino-6-chloro-2-(3-methylphenylmethylthio)-pyrimidine | 97–99 |
| Ex./Cpd #37 | 4-amino-6-chloro-2-(4-methylphenylmethylthio)-pyrimidine | 95–96 |
| Ex./Cpd #38 | 4-amino-6-chloro-2-(3-trifluoromethylphenylmethylthio)-pyrimidine | 95–96 |
| Ex./Cpd #39 | 4-amino-6-chloro-2-(3-methoxyphenylmethylthio)-pyrimidine | 100 |
| Ex./Cpd #40 | 4-amino-6-chloro-2-(4-methoxyphenylmethylthio)-pyrimidine | 118–120 |
| Ex./Cpd #41 | 4-amino-6-chloro-2-(3-fluorophenylmethylthio)-pyrimidine | 97–99 |
| Ex./Cpd #42 | 4-amino-6-chloro-2-(3-chlorophenylmethylthio)-pyrimidine | 103–105 |
| Ex./Cpd #43 | 4-amino-6-chloro-2-(3-bromophenylmethylthio)-pyrimidine | 91–93 |
| Ex./Cpd #44 | 4-amino-6-chloro-2-(3-iodophenylmethylthio)-pyrimidine | 109 |
| Ex./Cpd #45 | 4-amino-6-chloro-2-(3-nitrophenylmethylthio)-pyrimidine | 117–119 |
| Ex./Cpd #46 | 4-amino-6-chloro-2-(3-carbomethoxyphenylmethylthio)-pyrimidine | 169–171 |
| Ex./Cpd #47 | 4-amino-6-chloro-2-(4-t-butylphenylmethylthio)-pyrimidine | 124–126 |
| Ex./Cpd #48 | 4-amino-6-chloro-2-(3,4-difluorophenylmethylthio)-pyrimidine | 123–125 |
| Ex./Cpd #49 | 4-amino-6-chloro-2-(3,4-dichlorophenylmethylthio)-pyrimidine | 172 |
| Ex./Cpd #50 | 4-amino-6-chloro-2-(3,5-dichlorophenylmethylthio)-pyrimidine | 166–168 |
| Ex./Cpd #51 | 4-amino-6-chloro-2-(2,4-dichlorophenylmethylthio)-pyrimidine | 144–147 |
| Ex./Cpd #52 | 4-amino-6-chloro-2-(3,5-dibromophenylmethylthio)-pyrimidine | 184–186 |
| Ex./Cpd #53 | 4-amino-6-chloro-5-cyclohexyl-2-(benzylthio)-pyrimidine | 149–151 |
| Ex./Cpd #54 | 4-amino-6-chloro-5-isopropyl-2-(benzylthio)-pyrimidine | 83–85 |
| Ex./Cpd #55 | 4-amino-6-chloro-2-(2-pyridylmethylthio)-pyrimidine | 185–187 |
| Ex./Cpd #56 | 4-amino-6-chloro-2-[2-(3-ethoxy)pyridylmethylthio]-pyrimidine | 151.5–154 |
| Ex./Cpd #57 | 4-amino-6-chloro-2-(3-pyridylmethylthio)-pyrimidine | 159–161 |
| Ex./Cpd #58 | 4-amino-6-chloro-2-(1-naphthylmethylthio)-pyrimidine | 114–117 |
| Ex./Cpd #59 | 4-amino-6-chloro-2-(2-naphthylmethylthio)-pyrimidine | 98–101 |
| Ex./Cpd #60 | 4-amino-6-chloro-2-(6,7-difluoro-2-naphthylmethylthio)-pyrimidine | 125–127 |

-continued

|  |  | mp (° C.) |
|---|---|---|
| Ex./Cpd #61 | 4-amino-6-chloro-2-(2-quinolinylmethylthio)-pyrimidine | 150–152 |
| Ex./Cpd #62 | 4-amino-6-chloro-2-(6-chloro-5-piperonylmethylthio)-pyrimidine | 157–159 |
| Ex./Cpd #64 | 4-amino-6-chloro-2-(E-styrylmethylthio)-pyrimidine | 117–120 |
| Ex./Cpd #65 | 4-chloro-2-(2-naphthylmethylthio)-pyrimidine | 76–78 |
| Ex./Cpd #66 | 4-amino-6-chloro-2-(propargylthio)-pyrimidine | 137–140 |

Example 67

Preparation of 4-amino-6-chloro-2-(3-bromophenylmethylsulfmyl)-pyrimidine; (Cpd #67)

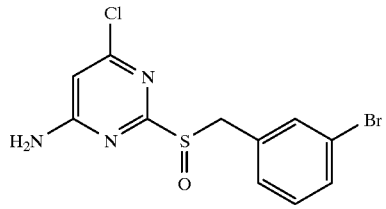

4-amino-6-chloro-2-(3-bromophenylmethylthio)-pyrimidine (165 mg, 0.5 mmol; Cpd #43) in methylene chloride (10 ml) is treated with 50% mCPBA (172 mg, 0.50 mmol) and stirred for 17 hours. The solid is collected by filtration, washed with ether, and dried, mp 216–217° C.

Following the procedure of Example 67 and making noncritical changes, but starting with 4-amino-6-chloro-2-(2-naphthylmethylthio)-pyrimidine (Cpd #59), the compound 4-amino-6-chloro-2-(2-naphthylmethylsulfmyl)-pyrimidine (Cpd #68) is prepared (mp 222–223° C.).

Example 69

Preparation of 4-amino-6-chloro-2-(3-bromophenylmethylsulfonyl)-pyrimidine (Cpd #69)

4amino-6-chloro-2-(3-bromophenylmethylthio)-pyrimidine (660 mg, 2.0 mmol; Cpd #43) in acetic acid (5 ml) is treated with 30% $H_2O_2$ (1 ml) and stirred at rt for 72 hours. The crude product is diluted with ethyl acetate, washed with water, sat'd $NaHCO_3$ and brine, dried with $MgSO_4$, then concentrated in vacuo. The material is purified by chromatography using 1:1 ethyl acetate/hexanes, mp 191–192° C.

Example 70

Preparation of 4-amino-5-bromo-6-chloro-2-(2-naphthylmethylthio)-pyrimidine; (Cpd #70)

4-amino-6-chloro-2-(2-naphthylmethylthio)-pyrimidine (302 mg, 1.0 mmol; Cpd #59) and $NaHCO_3$ (100 mg, 1.2 mmol) are dissolved in 50% methanol (3 ml) and treated dropwise with a solution of bromine in methanol (0.92 M, 1.2 ml, 1.1 mmol). The reaction is decolorized with sat'd $NaHSO_3$ and extracted with ethyl acetate. The organic fraction is washed with water, dried with $MgSO_4$, then concentrated in vacuo. The material is purified by chromatography using 15:85 ethyl acetate/hexanes, mp 158° C.

Following the general procedure of Example 70 and making noncritical changes, 4amino-5-bromo-6-chloro-2-(2-pyridylmethylthio)-pyrimidine (Cpd #71; mp 119–120° C.) is prepared from 4amino-6-chloro-2-(2-pyridylmethylthio)-pyrimidine (Cpd #55).

Example 72

Preparation of 4,6 dihydroxy-2-(phenylmethylthio)-pyrimidine

Thiobarbituric acid (5.22 g, 36.2 mmol) in ethanol (52 ml) is treated with 3.25 M NaOH (11.1 ml, 36.2 mmol) and the mixture heated to reflux for 30 minutes. After cooling the reaction mixture briefly, benzyl bromide (4.3 ml, 36.2 mmol) is added and the solution is heated to reflux for one hour. The reaction mixture was cooled and concentrated in vacuo, and the resultant white solid is filtered and washed with cold $H_2O$ followed by cold ethanol, mp >320° C.

Following the general procedure of Example 72 and making noncritical changes, but beginning with the appropriate dihydroxy pyrimidine thione, the following compounds are synthesized:

|  |  | mp (° C.) |
|---|---|---|
| Ex./Cpd #73 | 4,6-dihydroxy-5-methoxy-2-(2-naphthylmethylthio)-pyrimidine | 248–249 |
| Ex./Cpd #74 | 4,6-dihydroxy-5-fluoro-2-(2-naphthylmethylthio)-pyrimidine | >325 |
| Ex./Cpd #75 | 4,6-dihydroxy-5-methyl-2-(2-naphthylmethylthio)-pyrimidine | 285–286 |
| Ex./Cpd #76 | 4,6-dihydroxy-5-fluoro-2-(2-pyridylmethylthio)-pyrimidine | 195(d) |
| Ex./Cpd #77 | 4,6-dihydroxy-2-(4-methoxyphenylmethylthio)-pyrimidine | 207–208 |

Example 78

Preparation of 4,6-dichloro-2-(benzylthio)-pyrimidine (Cpd #78)

2-(Benzylthio)-4,6-dihydroxypyrimidine (5.95 g, 25.4 mmol; Cpd #72) is treated with $POCl_3$ (26 ml) and heated to reflux for 2 hours. The reaction is cooled and excess $POCl_3$ is removed by distillation in vacuo. The hot residue is poured onto ice and the aqueous layer is neutralized with solid NaOH to pH 7–8. The aqueous solution is extracted with ethyl acetate three times and the combined organics are washed dilute NaOH and brine, then dried with $MgSO_4$. The solution is filtered and concentrated in vacuo then purified by distillation, BP (0.2 mmHg) 155–160 C. to yield the title compound.

NMR: ($CDCl_3$) 7.43 (m, 2H), 7.29 (m, 3H), 7.02 (s, 1H), 4.37 (s, 2H).

Following the general procedure of Example 78 and making noncritical changes, but beginning with the appropriate dihydroxy pyrimidine, the following compounds are synthesized:

|  | mp (° C.) |
|---|---|
| Ex./Cpd #79 4,6-dichloro-5-methoxy-2-(2-naphthylmethylthio)-pyrimidine | 93–94 |
| Ex./Cpd #80 4,6-dichloro-5-fluoro-2-(2-naphthylmethylthio)-pyrimidine | 80–81 |
| Ex./Cpd #81 4,6-dichloro-5-methyl-2-(2-naphthylmethylthio)-pyrimidine | 109–110 |
| Ex./Cpd #82 4,6-dichloro-5-fluoro-2-(2-pyridylmethylthio)-pyrimidine | NMR |
| Ex./Cpd #83 4,6-dichloro-2-(4-methoxyphenylmethylthio)-pyrimidine | 39–42 |

Cpd #82: NMR: (CDCl$_3$) 8.58 (d, J=4.1, 1H), 7.67 (m, 1H), 7.50 (m, 1H), 7.24 (m, 1H), 4.51 (s, 2H).

Example 84

Preparation of 4-piperido-6-chloro-2-(benzylthio)-pyrimidine; Cpd #84

4,6-dichloro-2-(benzylthio)-pyrimidine (261 mg, 0.96 mmol; Cpd 78) is dissolved in methylene chloride (3 ml), treated with triethyl amine (0.17 ml, 1.20 mmol) and piperidine (0.10 ml, 1.06 mmol) and stirred at rt for 60 hours. The reaction is quenched with sat'd NH$_4$Cl, washed with sat'd NaHCO$_3$, dried with MgSO$_4$ and concentrated in vacuo. The sample is purified by chromatography using 1:3 ethyl acetate/hexanes, mp 85–86° C.

Following the general procedure of Example 84 and making noncritical changes, but beginning with the appropriately substituted amine, the following compounds are synthesized:

|  |  | mp (° C.) |
|---|---|---|
| Ex./Cpd #85 | 4-pyrrolidino-6-chloro-2-(benzylthio)-pyrimidine | 80–81 |
| Ex./Cpd #86 | 4-morpholino-6-chloro-2-(benzylthio)-pyrimidine | 119–120 |
| Ex./Cpd #87 | 4-propylamino-6-chloro-2-(benzylthio)-pyrimidine | 67–68 |
| Ex./Cpd #88 | 4-hydrazino-6-chloro-2-(benzylthio)-pyrimidine | 136–138 |

Example 89

Preparation of 4-amino-5-methoxy-6-chloro-2-(2-naphthylmethylthio)-pyrimidine (Cpd #89)

4,6-dichloro-5-methoxy-2-(2-naphthylmethylthio)-pyrimidine (1.40 g, 4.0 mmol; Cpd #79) is dissolved in acetonitrile (10 ml), treated with concentrated ammonium hydroxide (2 ml), then heated to 120 C. in a sealed tube for 2.5 hrs. After cooling, the product is filtered, washed with water, and dried, mp 115–117° C.

Following the general procedure of Example 89 and making noncritical changes, but beginning with the appropriate dichloropyrimidine, the following compounds are synthesized:

|  | mp (° C.) |
|---|---|
| Ex./Cpd #90 4-amino-5-methyl-6-chloro-2-(2-naphthylmethylthio)-pyrimidine | 156 |
| Ex./Cpd #91 4-amino-5-fluoro-6-chloro-2-(2-naphthylmethylthio)-pyrimidine | 160 |
| Ex./Cpd #92 4-amino-5-fluoro-6-chloro-2-(2-pyridylmethylthio)-pyrimidine | 171–172 |
| Ex./Cpd #93 4-amino-6-chloro-2-(4-methoxyphenylmethylthio)-pyrimidine | 118.5–119.5 |

Example 94

Preparation of 4-amino-2-(2-pyridylmethylthio)-pyrimidine; Cpd #94

4-Amino-2-mercaptopyrimidine (0.40 g, 3.15 mmol) is slurried in ethanol (2 ml) and 3.25 M NaOH (2.0 ml, 6.5 mmol) is added. The solution is heated to reflux for 10 minutes and after cooling to 22° C., 2-picolyl chloride*HCl (0.49 g, 2.98 mmol) is added. The solution is heated to reflux for an additional 15 minutes. The solution is cooled and concentrated in vacuo. The residue is dissolved in 1 N HCl and diluted with ethyl acetate. The mixture is neutralized with NaOH to pH 8 and the aqueous layer is separated and washed twice with ethyl acetate. The combined organic layers are washed with saturated NaHCO$_3$, saturated NaCl, dried with MgSO$_4$ and concentrated in vacuo, mp 133–134° C.

Following the general procedure of Example 94 and making noncritical changes, but beginning with the appropriate thiol, the following compounds are synthesized:

|  | mp (° C.) |
|---|---|
| Ex./Cpd #95 4-amino-2-(3-bromophenylmethylthio)-pyrimidine | 111–112 |
| Ex./Cpd #96 4-amino-2-(3-methylphenylmethylthio)-pyrimidine | 88–89 |

| | | mp (° C.) |
|---|---|---|
| Ex./Cpd #97 | 4-amino-2-(3-pyridylmethylthio)-pyrimidine | 118–119 |
| Ex./Cpd #98 | 4-amino-2-(2-naphthylmethylthio)-pyrimidine | 115–116 |
| Ex./Cpd #99 | 4-amino-6-chloro-2-(2-benzothiazolomethylthio)-pyrimidine | 202–203 |
| Ex./Cpd #100 | 4-amino-6-chloro-2-[2-(1-phenyl-1-ethanon)thio]-pyrimidine | 194–195 |
| Ex./Cpd #101 | 4-amino-6-chloro-2-(cyclohex-1-enylmethylthio)-pyrimidine | 122–123 |
| Ex./Cpd #102 | 4-amino-6-chloro-2-(Z-styrylthio)-pyrimidine | |

Example 103

Preparation of 4-amino-6-chloro-2-(1-naphthylmethyloxy)-pyrimidine;

1-Naphthalenemethanol (227 mg, 1.44 mmol) is added to a slurry of 50% sodium hydride (69 mg, 1.44 mmol) in dry THF (4 ml) at 0° C. After stirring for 30 minutes, 4-amino-2,6-dichloropyrimidine (157 mg, 0.96 mmol) is added and stirred at 22° C. for 72 hours. The solution is quenched with saturated $NH_4Cl$ and concentrated in vacuo. The residue is dissolved in methylene chloride and washed 3x saturated $NaHCO_3$, dried with $MgSO_4$, filtered, and concentrated in vacuo. The sample is purified by chromatography using 1:2 ethyl acetate/hexanes and recrystallization from heptane/toluene, mp 160–161° C.

Following the general procedure of Example 103 and making noncritical changes, but beginning with the appropriate alcohol, the following compounds are synthesized:

| | | mp (° C.) |
|---|---|---|
| Ex./Cpd #104 | 4-amino-6-chloro-2-(benzyloxy)-pyrimidine | 114–115 |
| Ex./Cpd #105 | 4-amino-6-chloro-2-(2-naphthylmethyloxy)-pyrimidine | 130–131 |
| Ex./Cpd #106 | 4-amino-6-chloro-2-(3-methylphenylmethyloxy)-pyrimidine | 85–87 |
| Ex./Cpd #107 | 4-amino-6-chloro-2-(3-bromophenylmethyloxy)-pyrimidine | 96–98 |

Example 108

Preparation of 4-amino-6-chloro-2-(3-hydroxyphenylmethylthio)-pyrimidine 4-amino-6-chloro-2-(3-methoxyphenylmethylthio)-pyrimidine (36 mg, 0.128 mmol; Cpd #39) is dissolved in methylene chloride (0.25 ml), cooled to 0° C. and treated with a solution of $BBr_3$ (0.32 ml, 0.32 mmol, 1M in methylene chloride). The reaction is stirred at 0° C. for 20 min, then refluxed for 2 hrs. After cooling, the reaction is quenched with water, and refluxed for an additional 30 min. Upon cooling the solid is collected and purified by recrystallization from ethanol/water, mp 147.5–148.5° C.

Example 109

Preparation of 4-amino-6-chloro-2-(3-isopropoxyphenylmethylthio)-pyrimidine (Cpd #108)

4-amino-6-chloro-2-(3-hydroxyphenylmethylthio)-pyrimidine (135 mg, 0.50 mmol; Cpd 108) is added to a solution of KOH (280 mg, 5 mmol) in DMSO (2.5 ml) at room temperature. 2-Bromopropane (615 mg, 5 mmol) is added and the reaction stirred overnight, then poured onto water. The aqueous solution is extracted with ethyl acetate, dried with $MgSO_4$, filtered, and concentrated in vacuo. The sample is purified by chromatography using 1:3 ethyl acetate/hexanes, mp 71° C.

Example 110

Preparation of 4amino-6-chloro-2-thio-pyrimidine (Cpd #110)

4-amino-6-chloro-2-(4-methoxyphenylmethylthio)-pyrimidine (11.0 g, 39.15 mmol: Cpd #93) and trifluoroacetic acid (84 ml) are heated to reflux for 20 hours, then the excess solvent is removed in vacuo. The sample is triturated with chloroform then stirred with ether and filtered. The solid is washed with ether then air dried, mp >320° C.

Example 111

Preparation of 4-amino-6-chloro-2-[2-(4-chloro)-pyridylmethylthio]-pyrimidine (Cpd #111)

4-Amino-6-chloro-2-thio-pyrimidine (Cpd #110; 614 mg, 2.38 mmol) in ethanol (1.5 ml) is treated with 3.25 M NaOH (1.47 ml, 4.8 mmol) and the mixture is warmed to 50° C. 4-chloro-2-chloromethyl pyridine is added and the solution is stirred warm for 1 hour. The reaction mixture is cooled and concentrated in vacuo, and the resultant solid is filtered and washed with water followed by cold ethanol, mp 195° C.

Following the general procedure of Example 111 and making noncritical changes, but beginning with the appropriate chloromethylarene, the following compounds are synthesized:

| | | mp (° C.) |
|---|---|---|
| Ex./Cpd #112 | 4-amino-6-chloro-2-[2-(6-chloro)pyridylmethylthio]-pyrimidine | 135–136 |
| Ex./Cpd #113 | 4-amino-6-chloro-2-[2-(6-methyl)pyridylmethylthio]-pyrimidine | 156–157 |
| Ex./Cpd #114 | 4-amino-6-chloro-2-[2-(4-methyl)pyridylmethylthio]-pyrimidine | 192–193 |
| Ex./Cpd #115 | 4-amino-6-chloro-2-[2-(4-ethoxy)pyridylmethylthio]-pyrimidine | 181–185 |
| Ex./Cpd #116 | 4-amino-6-chloro-2-[2-(4-thiophenyl)pyridylmethylthio]-pyrimidine | 136–137 |
| Ex./Cpd #117 | 4-amino-6-chloro-2-[2-(3-methyl)pyridylmethylthio]-pyrimidine | 148–149 |
| Ex./Cpd #118 | 4-amino-6-chloro-2-[2-(5-methyl)pyridylmethylthio]-pyrimidine | 191–192 |
| Ex./Cpd #119 | 4-amino-6-chloro-2-[2-(4-bromo)pyridylmethylthio]-pyrimidine | 188d |
| Ex./Cpd #120 | 4-amino-6-chloro-2-[2-(4-methoxy-6-methyl)-pyridylmethylthio]-pyrimidine | 171–172 |
| Ex./Cpd #121 | 4-amino-6-chloro-2-[2-(4,6-dimethyl)pyridylmethylthio]-pyrimidine | 160–161 |
| Ex./Cpd #122 | 4-amino-6-chloro-2-[2-(4-ethyl)pyridylmethylthio]-pyrimidine | 173–174 |
| Ex./Cpd #123 | 4-amino-6-chloro-2-[2-(4-methoxy)pyridylmethylthio]-pyrimidine | 191–192 |
| Ex./Cpd #124 | 4-amino-6-chloro-2-[2-(4-(2-methylpropyl))pyridylmethylthio]-pyrimidine | 156–157 |
| Ex./Cpd #125 | 4-amino-6-chloro-2-[2-(6-chloro-4-methyl)pyridylmethylthio]-pyrimidine | 171–172 |
| Ex./Cpd #126 | 4-amino-6-chloro-2-[2-(4-isopropoxy)pyridylmethylthio]-pyrimidine | 168–169 |
| Ex./Cpd #127 | 4-amino-6-chloro-2-[2-(4,6-dimethyl)pyrimidinylmethylthio]-pyrimidine | 180–181 |
| Ex./Cpd #128 | 4-amino-6-chloro-2-[2-(4-cyano)pyridylmethylthio]-pyrimidine | 214–215 |
| Ex./Cpd #130 | 4-amino-6-chloro-2-[4-(6-methyl)pyrimidinylmethylthio]-pyrimidine | 165–166 |
| Ex./Cpd #131 | 4-amino-6-chloro-2-[2-(4-propyl)pyridylmethylthio]-pyrimidine | 161–162 |
| Ex./Cpd #132 | 4-amino-6-chloro-2-[2-(4-isopropyl)pyridylmethylthio]-pyrimidine | 139 |
| Ex./Cpd #133 | 4-amino-6-chloro-2-[2-(5-phenyl)pyridylmethylthio]-pyrimidine | 191 |
| Ex./Cpd #134 | 4-amino-6-chloro-2-[2-(4-ethyl)pyridylmethylthio]-pyrimidine | 180 |
| Ex./Cpd #135 | 4-amino-6-chloro-2-[2-(4-(α-hydroxy, α-methyl)ethyl)pyridyl-methylthio]-pyrimidine | 140–143 |
| Ex./Cpd #137 | 4-amino-6-chloro-2-[2-(4-cyclopropyl)pyridylmethylthio]-pyrimidine | 162–163 |
| Ex./Cpd #138 | 4-amino-6-chloro-2-[2-(4-cyclopentyl)pyridylmethylthio]-pyrimidine | 138–139 |
| Ex./Cpd #140 | 4-amino-6-chloro-2-[2-(4,5-dimethyl)pyridylmethylthio]-pyrimidine | 210–211 |
| Ex./Cpd #142 | 4-amino-6-chloro-2-[4-(2,6-dimethyl)pyrimidinylmethylthio]-pyrimidine | 132–138 |
| Ex./Cpd #143 | 4-amino-6-chloro-2-[2-(4-pyrrolidino)pyridylmethylthio]-pyrimidine | 205d |
| Ex./Cpd #144 | 4-Amino-6-chloro-2-[(5-chlorothiophen-2-ylmethyl)thio]pyrimidine | 100–102 |
| Ex./Cpd #145 | 4-amino-6-chloro-2-[2-(4-(2-butyl))pyridylmethylthio]-pyrimidine | 115–117 |
| Ex./Cpd #146 | 4-amino-6-chloro-2-[2-(4-dimethylamino)pyridylmethylthio]-pyrimidine | 207–208 |
| Ex./Cpd #147 | 2-[2-(4-amino-6-chloro)pyrimidinylthiomethyl]-pyridine-1-oxide | 199–200d |
| Ex./Cpd #148 | 4-Amino-6-chloro-2-[(furan-3-ylmethyl)thio]pyrimidine | 83–84 |
| Ex./Cpd #149 | 4-amino-6-chloro-5-fluoro-2-[2-(4-chloro)pyridylmethylthio]pyrimidine | 172 |
| Ex./Cpd #151 | 4-amino-6-chloro-2-[2-(4-(3-pentyl))pyridylmethylthio]-pyrimidine | 144–145 |
| Ex./Cpd #152 | 4-amino-6-chloro-2-[2-(4-acetyl)pyridylmethylthio]-pyrimidine NMR: (CD$_3$OD)8.67(d, J=5.2, 1H), 8.12(s, 1H), 7.74(d, J=5.1, 1H), 6.22(s, 1H), 4.53(s, 2H), 2.64(s, 3H) | |
| Ex./Cpd #153 | 4-Amino-6-chloro-2-[(benzofuran-2-ylmethyl)thio]pyrimidine | 118–119 |
| Ex./Cpd #154 | 4-Amino-6-chloro-2-[2-(6-dimethylamino-4-methyl)pyridylmethylthio]-pyrimidine | 166–168 |
| Ex./Cpd #155 | 4-amino-6-chloro-2-[(1H-inden-3-ylmethyl)thio]pyrimidine NMR: (CDCl$_3$)7.47, 7.26, 6.54, 6.15, 4.99, 4.34, 3.37 | |
| Ex./Cpd #156 | 4-amino-6-chloro-2[2-(4-carbomethoxy)pyridylmethylthio]-pyrimidine | 168–169 |
| Ex./Cpd #157 | 4-Amino-6-chloro-2-[((S)-(-)perillyl)thio]pyrimidine | 115–116 |
| Ex./Cpd #158 | 4-Amino-6-chloro-2-[(benzothiophen-2-ylmethyl)thio]pyrimidine | 155–156 |
| Ex./Cpd #159 | 4-Amino-6-chloro-2-[(2H-1-benzopyran-3-ylmethyl)thio]pyrimidine | 110–113 |

Example #163

Preparation of 4-amino-6-chloro-2-[2-(4-carboxamido)pyridylmethylthio]-pyrimidine (Cpd#163)

4-amino-6-chloro-2-[2-(4-carbomethoxy) pyridylmethylthio]-pyrimidine (100 mg, 0.32 mmol) and freshly distilled formamide (48 mg, 1.06 mmol) are dissolved in THF (0.5 ml) and the solution is heated to reflux. Sodium methoxide (25%, 24 μl, 0.107 mmol) is added and the mixture is refluxed for 1 hour. The reaction is cooled and filtered through celite then concentrated in vacuo. The resultant solid is triturated with acetone. mp 191–192 ° C.

Example #164

Preparation of 4-amino-6-chloro-2-[2-(4-hydroxymethyl)-pyridylmethylthio]-pyrimidine (Cpd#164)

Lithium aluminum hydride (12 mg, 0.32 mmol) is suspended in THF (1 ml) and cooled to 0° C. The slurry is then treated with a solution of 4-amino-6-chloro-2-[2-(4-carbomethoxy)pyridylmethylthio]-pyrimidine (100 mg, 0.32 mmol) in THF (0.5 ml). The solution is allowed to warm to room temperature and stirred for 1 hour. The reaction is quenched with water (1 drop), 1 N NaOH (1 drop), and water (3 drops) and diluted with ethyl acetate. The reaction is dried with MgSO$_4$ and concentrated in vacuo. The resultant solid is triturated with ethyl acetate. mp 117–118° C.

Following the general procedure of Example 70 and making noncritical changes, but beginning with the appropriate 4-amino-6-chloro-2-[2-(4-substituted)-pyridylmethylthio]-pyrimidine, the following compounds are synthesized:

| | | mp (° C.) |
|---|---|---|
| Ex./Cpd #165 | 4-amino-5-bromo-6-chloro-2-[2-(4-methyl)pyridylmethylthio]-pyrimidine | 138–139 |
| Ex./Cpd #166 | 4-amino-5-bromo-6-chloro-2-[2-(4-isopropyl)pyridylmethylthio]-pyrimidine | 146–147 |

Following the general procedure of Example 111 and making noncritical changes, but beginning with the appropriate chloromethylarene, the following compounds are synthesized:

| | | |
|---|---|---|
| Ex./Cpd #167 | 4-amino-6-chloro-2-(2,6-dichlorophenyl)methylthio-pyrimidine | 173–174 |
| Ex./Cpd #168 | 4-Amino-6-chloro-2-[(2,3-dihydrobenzofuran-5-ylmethyl)thio]pyrimidine | 153 |
| Ex./Cpd #169 | 4-Amino-6-chloro-2-[(5-phenylisoxazol-3-ylmethyl)thio]pyrimidine | 217–219 |
| Ex./Cpd #170 | 4-Amino-6-chloro-2-[(2,3-dihydrobenzofuran-2-ylmethyl)thio]pyrimidine | 105–107 |
| Ex./Cpd #171 | 4-Amino-6-chloro-2-[[(3,4-dihydro-1-naphthalen-2-yl)methyl]thio]-pyrimidine | 104–105 |
| Ex./Cpd #172 | 4-Amino-6-chloro-2-[[(5-chloroimidazo[1,2-a]pyridin-2-yl)methyl]thio]-pyrimidine | >240 |
| Ex./Cpd #173 | 4-Amino-6-chloro-2-[(6-methylpyrazin-2-ylmethyl)thio]pyrimidine | 162 |
| Ex./Cpd #174 | 4-Amino-6-chloro-2-[(5-methylsoxazol-3-ylmethyl)thio]pyrimidine | 177–180 |
| Ex./Cpd #175 | 4-Amino-6-chloro-2-[(5-methylpyrazin-2-ylmethyl)thio]pyrimidine | 154–155 |
| Ex./Cpd #176 | 4-Amino-6-chloro-2-[(1-methylimidazol-2-ylmethyl)thio]pyrimidine | 178–180 |
| Ex./Cpd #177 | 4-Amino-6-chloro-2-[(3-methylpyrazin-2-ylmethyl)thio]pyrimidine | 162–163 |
| Ex./Cpd #178 | 4-Amino-6-chloro-2-[(quinolin-6-ylmethyl)thio]pyrimidine | 186–188(d) |
| Ex./Cpd #179 | 4-Amino-6-chloro-2-[(quinoxalin-2-ylmethyl)thio]pyrimidine | 195 (d) |
| Ex./Cpd #180 | 4-Amino-6-chloro-2-[(quinolin-8-ylmethyl)thio]pyrimidine | 174–175 |
| Ex./Cpd #181 | 4-Amino-6-chloro-2-[(quinolin-4-ylmethyl)thio]pyrimidine | 195 (d) |
| Ex./Cpd #182 | 4-Amino-6-chloro-2-[(isoquinolin-3-ylmethyl)thio]pyrimidine | >210 |
| Ex./Cpd #183 | 4-Amino-6-chloro-2-[(quinolin-5-ylmethyl)thio]pyrimidine | 190 (d) |
| Ex./Cpd #184 | 4-Amino-6-chloro-2-[(quinolin-7-ylmethyl)thio]pyrimidine | 195 (d) |
| Ex./Cpd #186 | 4-Amino-6-chloro-2-[(piperon-5-ylmethyl)thio]pyrimidine | 148–150 |
| Ex./Cpd #187 | 4-Amino-6-chloro-2-[[(3,4-dihydro-1-naphthalenyl)methyl]thio]pyrimidine | 127–130 |
| Ex./Cpd #188 | 4-amino-6-chloro-2[2-(5-carbomethyoxy)pyridylmethylthio]pyrimidine | 200 |
| Ex./Cpd #189 | 4-amino-6-chloro-2[2-(4-cyclohexyl)pyridylmethylthio)pyrimidine | 134 |

Following the general procedure of Example 72 and making noncritical changes, but beginning with the appropriate dihydroxy pyrimidine thione, the following compound is synthesized:

4,6-dihydroxy-5-fluoro-2-[2-(4-chloro) pyridylmethylthio]pyrimidine (Ex./Cpd #190)

NMR: (DMSO) 8.48 (d,J=5.5,1H), 7.71 (s,1H), 7.44 (s, 1H), 4.44 (s, 2H)

Following the general procedure of Example 78 and making noncritical changes, but beginning with the appropriate dihydroxy pyrimidine, the following compound is synthesized:

46-dichloro-5-fluoro-2-[2-(4-chloro) pyridylmethylthio]pyrimidine (Ex./Cpd #191)

NMR: (CDCl$_3$) 8.54 (d,J=5.5,1H), 7.77 (s, 1H), 7.39 (d, J=5.4,1H), 4.59 (s,2H)

| Example | IC50 | Example | IC50 | Example | IC50 |
|---|---|---|---|---|---|
| 34 | 10 | 50 | 0.33 | 85 | 30 |
| 34A | 2 | 51 | 1 | 86 | 40 |
| 35 | 0.3 | 52 | 0.2 | 87 | 100 |
| 36 | 0.05 | 53 | 15 | 88 | 5 |
| 37 | 0.33 | 55 | 0.002 | 89 | 5 |
| 38 | 1 | 57 | 10 | 90 | 5 |
| 39 | 0.16 | 58 | 0.03 | 91 | 2.5 |
| 41 | 0.2 | 59 | 0.036 | 92 | 1 |
| 42 | 0.5 | 60 | 10 | 95 | 1 |
| 43 | 0.14 | 61 | 5 | 96 | 50 |
| 44 | 0.6 | 62 | 0.02 | 98 | 5 |
| 45 | 0.11 | 64 | 0.066 | 99 | 0.5 |
| 46 | 0.1 | 67 | 25 | 100 | 2 |
| 47 | 1 | 68 | 5 | 109 | 2 |
| 48 | 0.5 | 69 | 20 | | |
| 49 | 0.06 | 84 | 10 | | |
| 111 | 0.03 | 128 | 1.00 | 149 | 0.05 |
| 112 | 0.07 | 130 | 0.8 | 151 | 0.06 |
| 113 | 0.09 | 131 | 0.05 | 152 | — |
| 114 | 0.01 | 132 | 0.02 | 153 | 10.00 |
| 115 | 0.05 | 133 | 1.00 | 154 | 0.05 |
| 116 | 10.00 | 134 | 0.05 | 155 | 5.00 |
| 117 | 1.05 | 135 | 0.1 | 156 | 0.1 |
| 118 | 0.07 | 137 | 0.01 | 157 | 10.00 |
| 119 | 0.04 | 138 | 0.12 | 158 | 1.00 |
| 120 | 0.02 | 140 | 0.02 | 159 | 0.5 |
| 121 | 0.01 | 142 | 0.5 | 163 | 20.00 |
| 122 | 0.01 | 143 | 0.05 | 164 | 1.00 |
| 123 | 0.05 | 144 | 5.00 | 165 | 0.05 |
| 124 | 40.00 | 145 | 0.01 | | |
| 125 | 0.05 | 146 | 0.01 | | |
| 126 | 0.05 | 147 | 5.00 | | |
| 127 | 1.0 | 148 | 10.00 | | |
| 166 | 0.02 | 175 | 8.0 | 183 | 0.04 |
| 167 | 5.00 | 176 | 25.0 | 184 | 3.0 |
| 168 | 0.05 | 177 | 37 @ 50 μM | 185 | 1.0 |
| 169 | 30 @ 50 μM | 178 | 0.5 | 186 | 0.5 |
| 170 | 32 @ 50 μM | 179 | 0.5 | 187 | 0.6 |

-continued
| Example | IC50 | Example | IC50 | Example | IC50 |
|---------|------|---------|------|---------|------|
| 171 | 1.0 | 180 | 0.5 | 188 | 50.00 |
| 172 | 50.0 | 181 | 1.0 | 189 | 1.00 |
| 173 | 10.0 | 182 | 0.02 | 192 | 0.02 |
| 174 | 0.5 | | | | |
FORMULAE
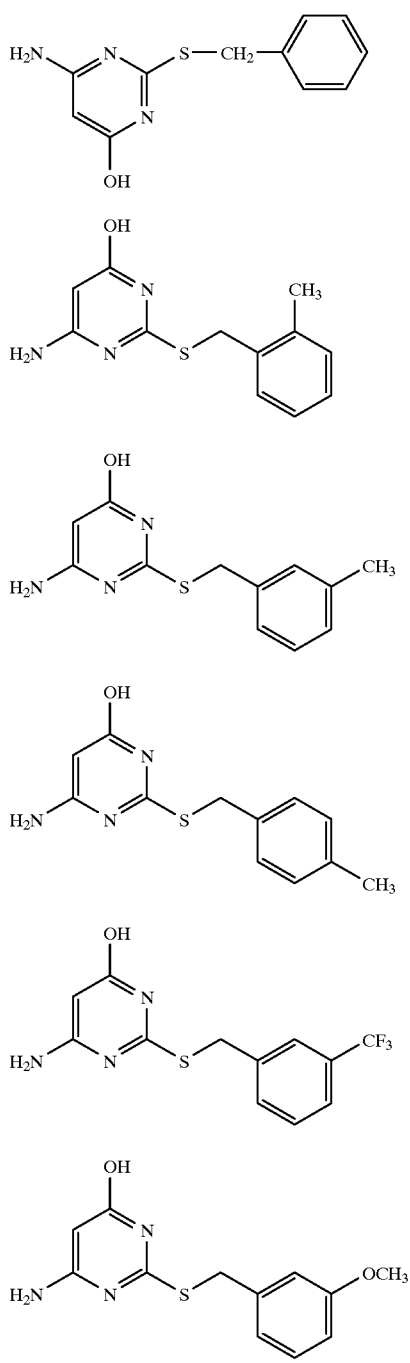
Cpd #2
Cpd #3
Cpd #4
Cpd #5
Cpd #6
Cpd #7
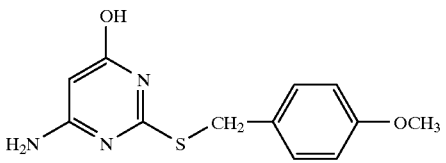
Cpd #8
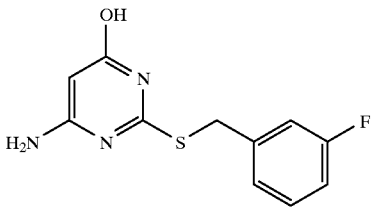
Cpd #9
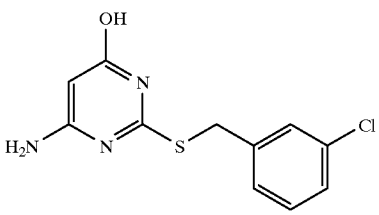
Cpd #10
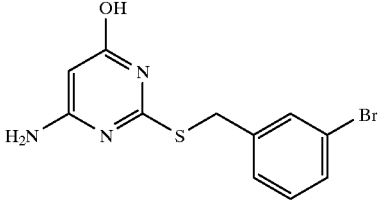
Cpd #11
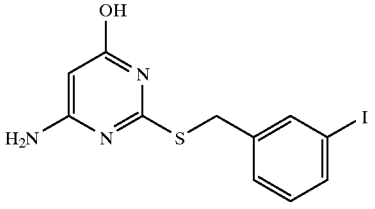
Cpd #12
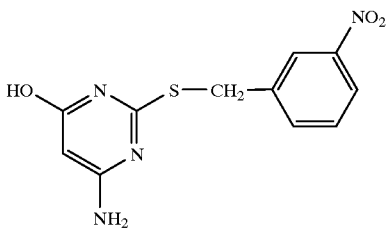
Cpd #13
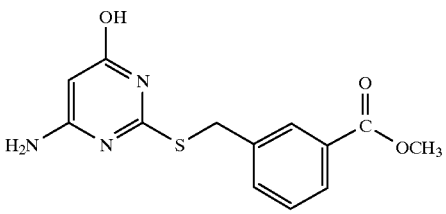
Cpd #14

Cpd #15
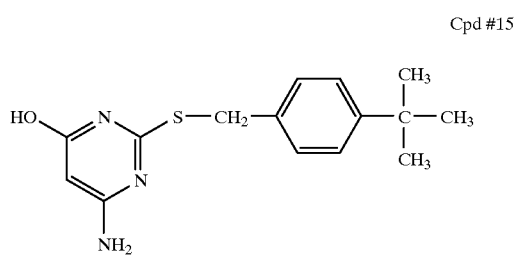
Cpd #16
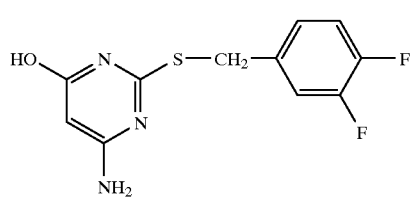
Cpd #17
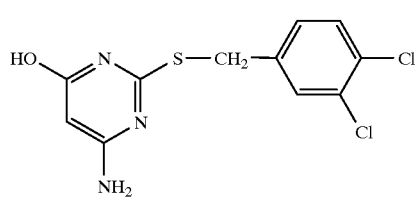
Cpd #18
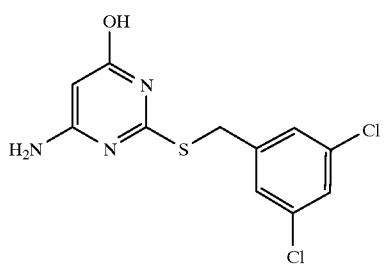
Cpd #19
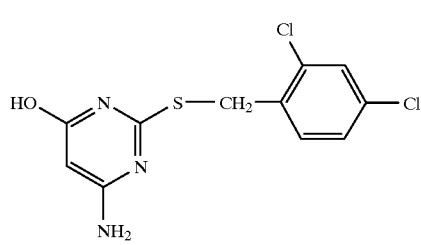
Cpd #20
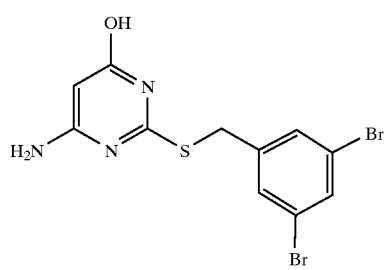
Cpd #21
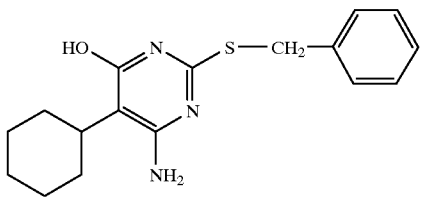
Cpd #22
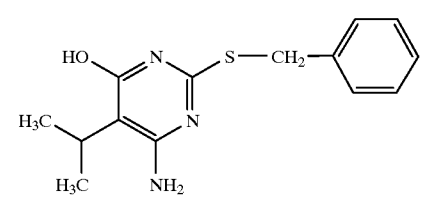
Cpd #23
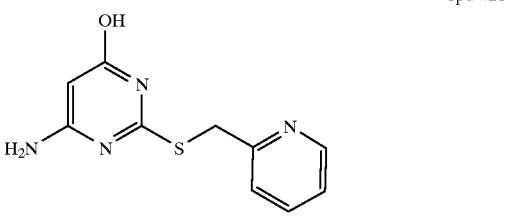
Cpd #24
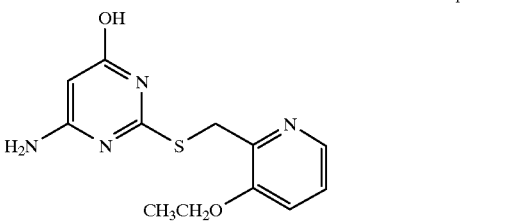
Cpd #25
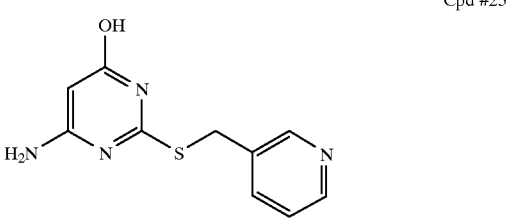
Cpd #26
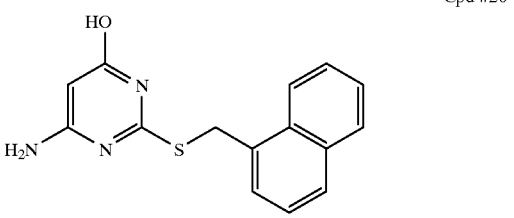
Cpd #27
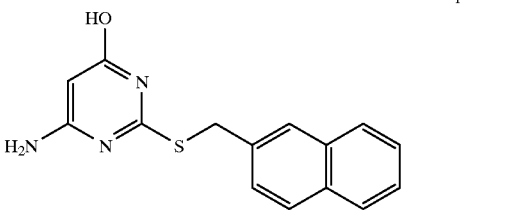

Cpd #28
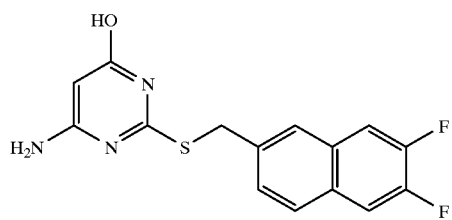
Cpd #29
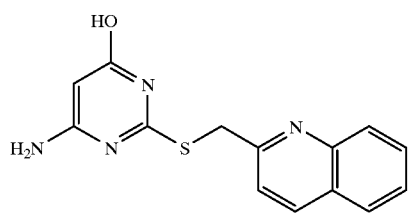
Cpd #30
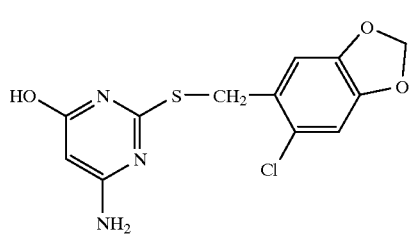
Cpd #32
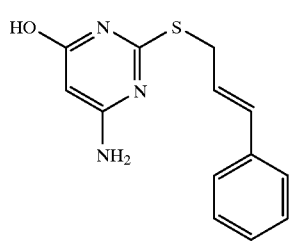
Cpd #33
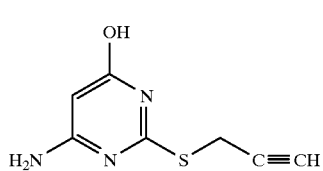
Cpd #34A
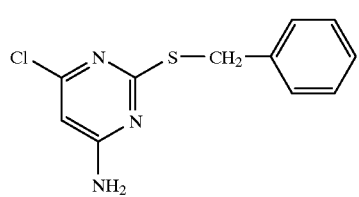
Cpd #35
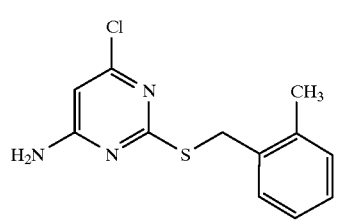
Cpd #36
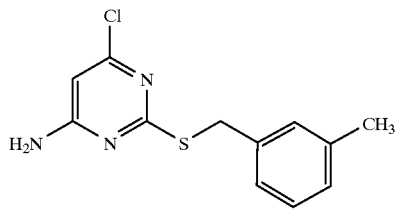
Cpd #37
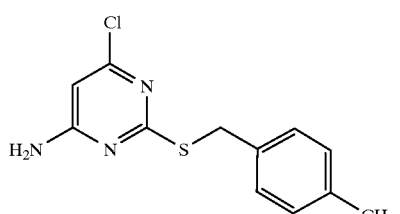
Cpd #38
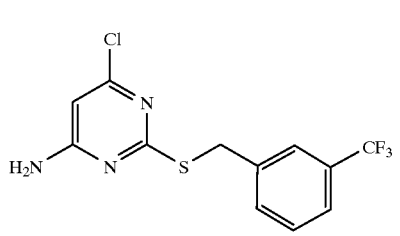
Cpd #39
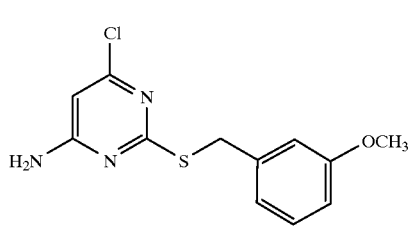
Cpd #40
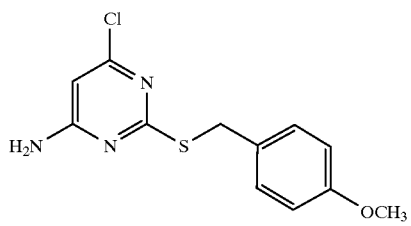
Cpd #41
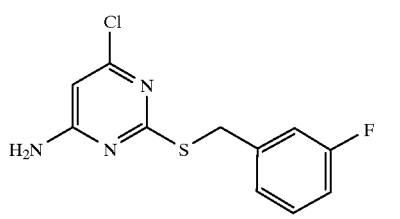

Cpd #42
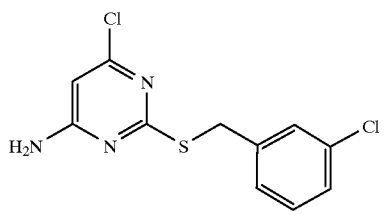
Cpd #43
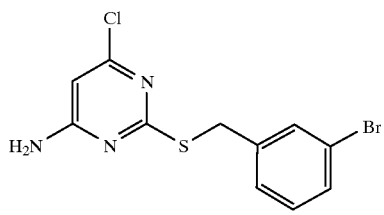
Cpd #44
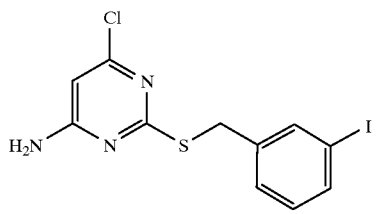
Cpd #45
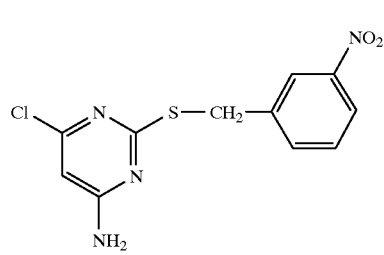
Cpd #46
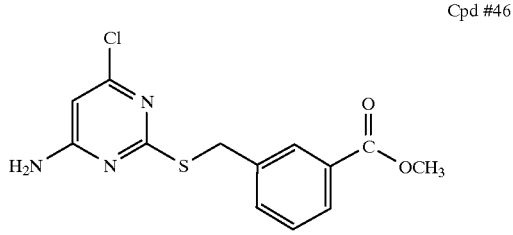
Cpd #47
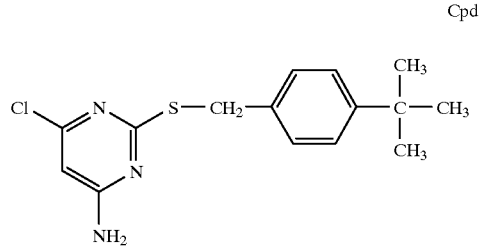
Cpd #48
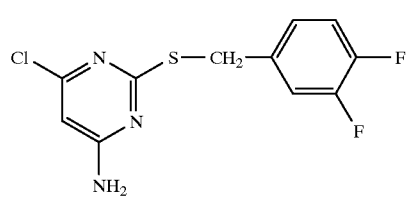
Cpd #49
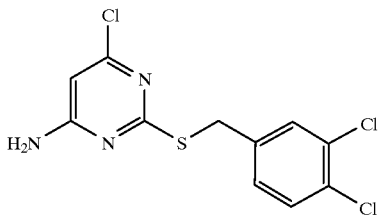
Cpd #50
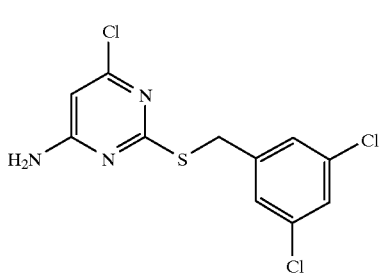
Cpd #51
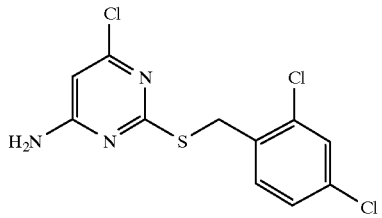
Cpd #52
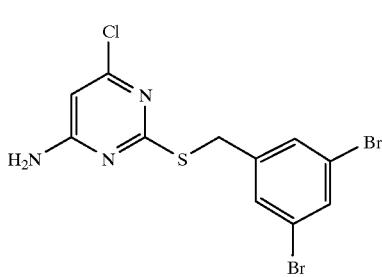
Cpd #53
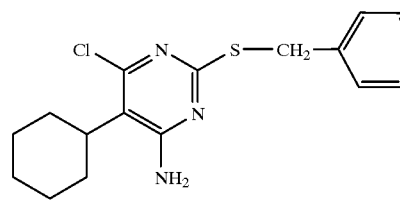
Cpd #54
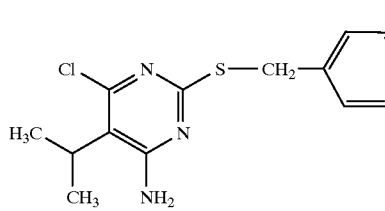

Cpd #55
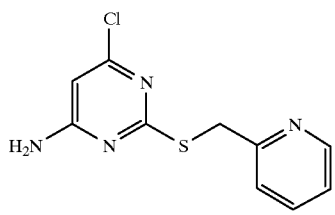
Cpd #56
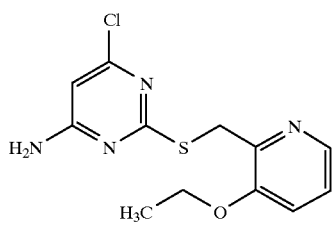
Cpd #57
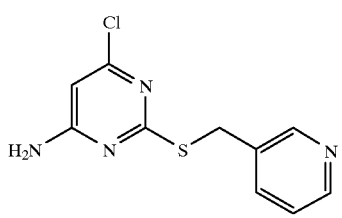
Cpd #58
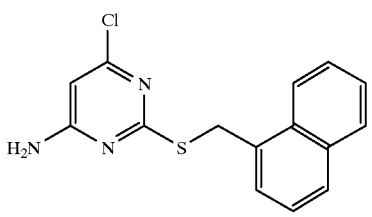
Cpd #59
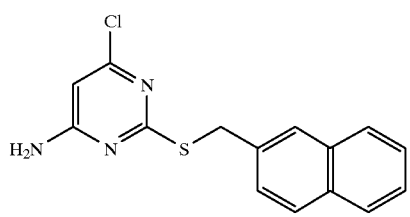
Cpd #60
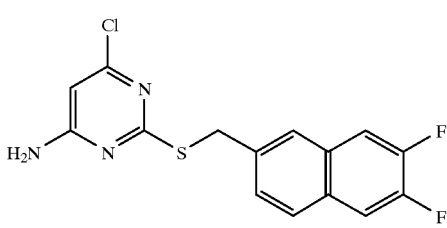
Cpd #61
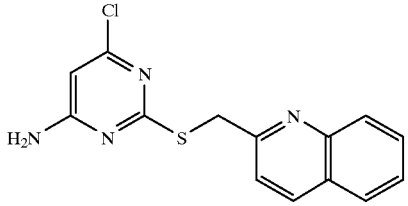
Cpd #62
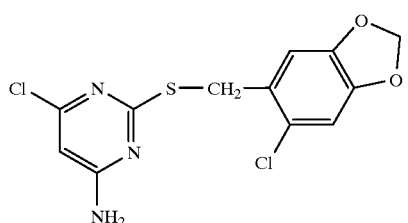
Cpd #64
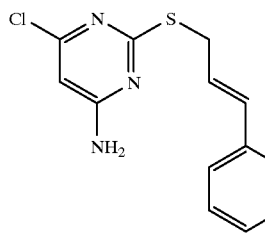
Cpd #65
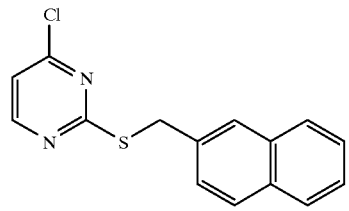
Cpd #66
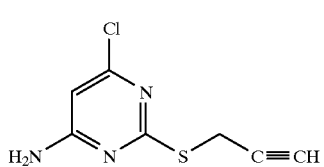
Cpd #67
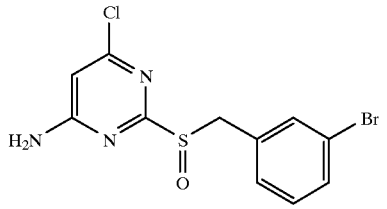
Cpd #68
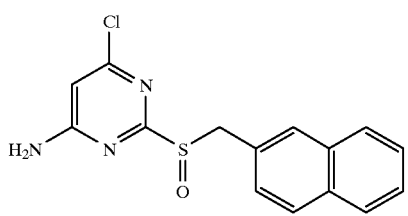

-continued

Cpd #69

Cpd #70

Cpd #71

Cpd #72

Cpd #73

Cpd #74

Cpd #75

-continued

Cpd #76

Cpd #77

Cpd #78

Cpd #79

Cpd #80

Cpd #81

Cpd #82

Cpd #83
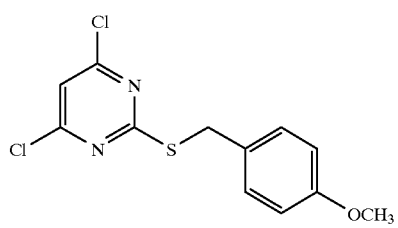
Cpd #84
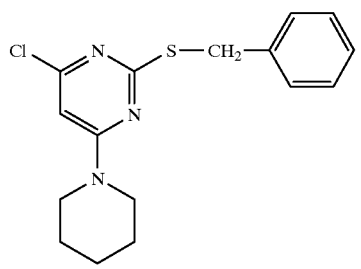
Cpd #85
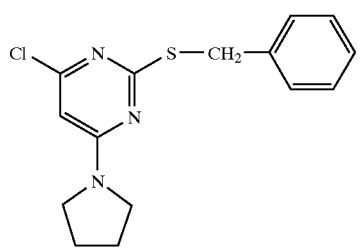
Cpd #86
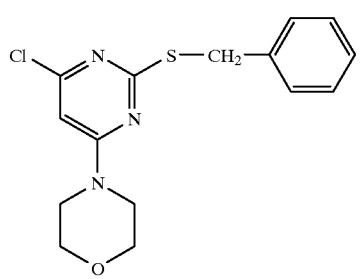
Cpd #87
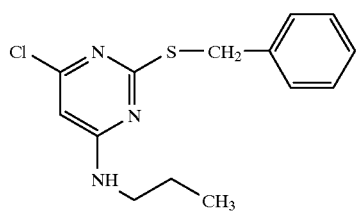
Cpd #88
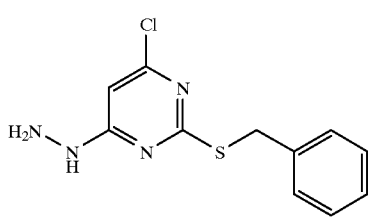
Cpd #89
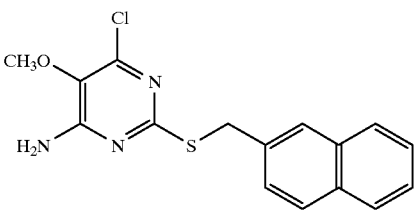
Cpd #90
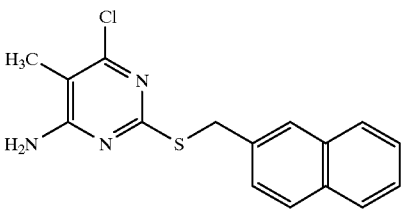
Cpd #91
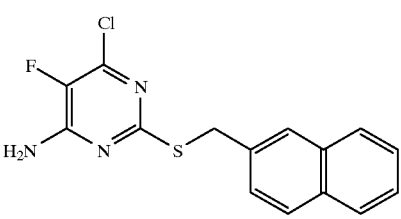
Cpd #92
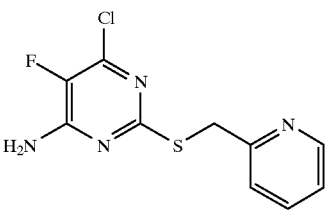
Cpd #93
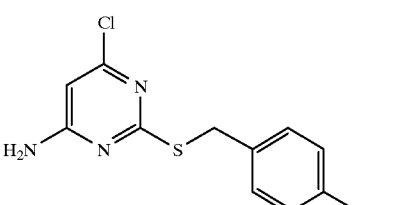
Cpd #94
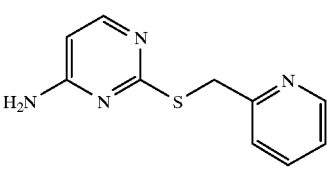
Cpd #95

Cpd #96
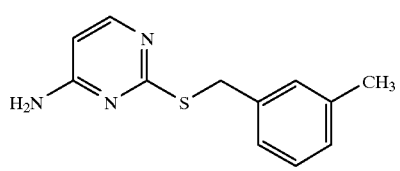
Cpd #97
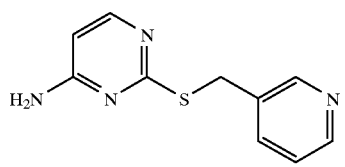
Cpd #98
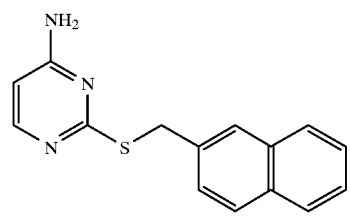
Cpd #99
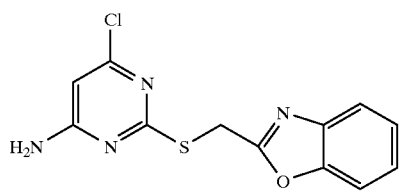
Cpd #100
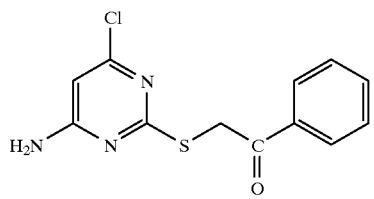
Cpd #101
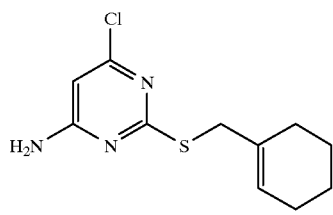
Cpd #102
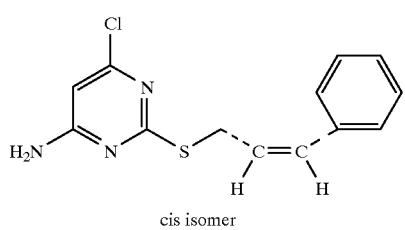
cis isomer
Cpd #103
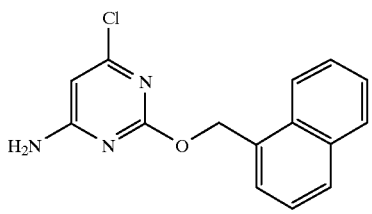
Cpd #104
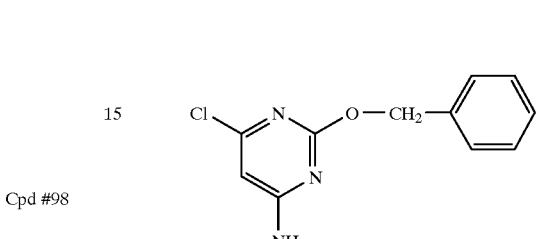
Cpd #105
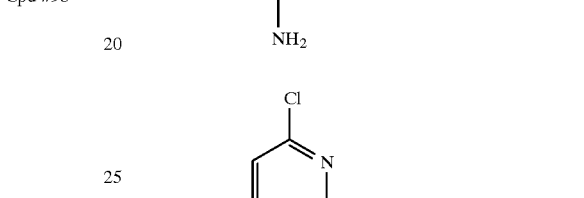
Cpd #106
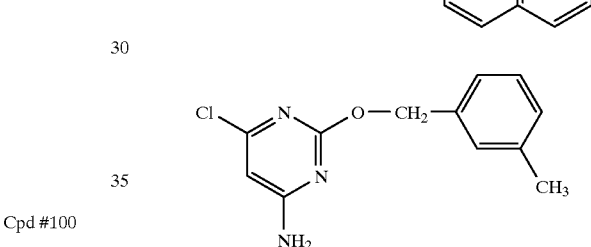
Cpd #107
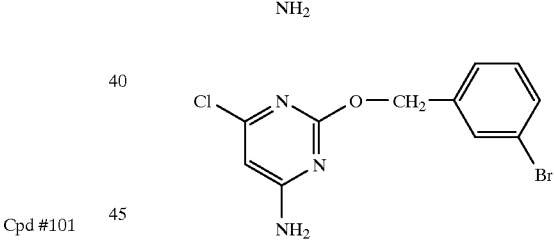
Cpd #108
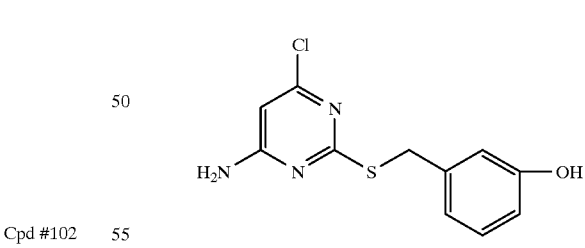
Cpd #109
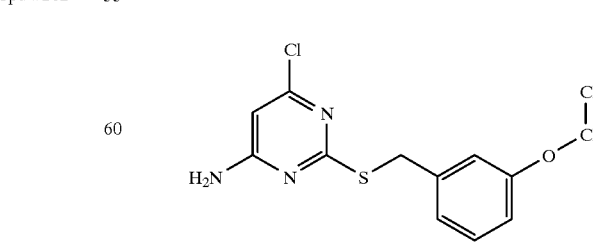

Cpd #110
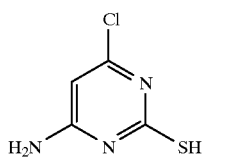
Cpd #111
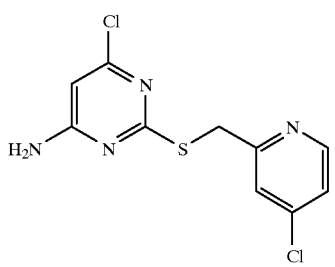
Cpd #112
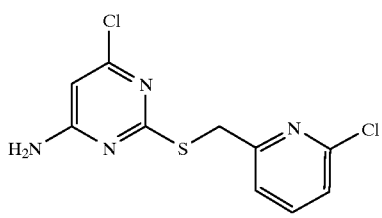
Cpd #113
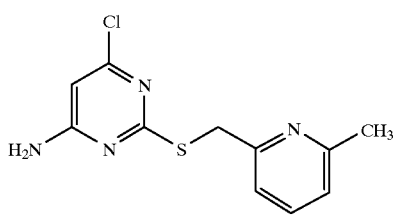
Cpd #114
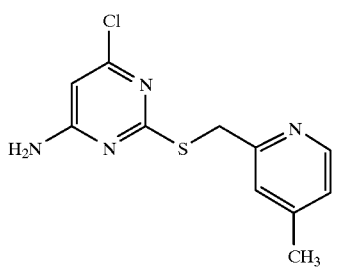
Cpd #115
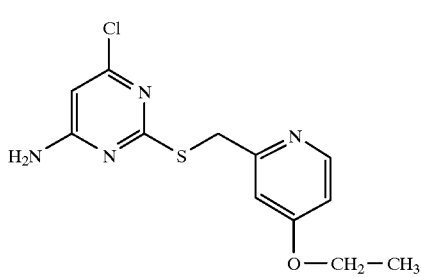
Cpd #116
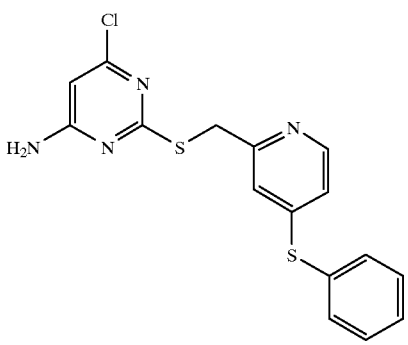
Cpd #117
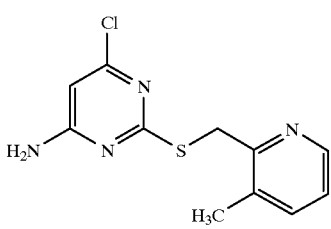
Cpd #118
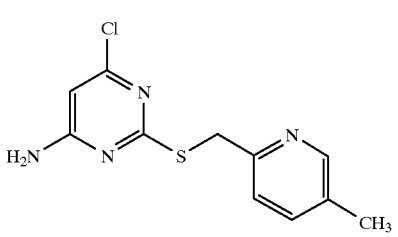
Cpd #119
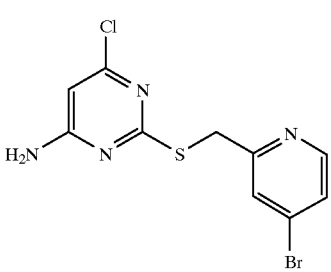
Cpd #120
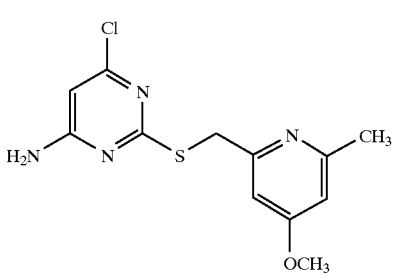

Cpd #121
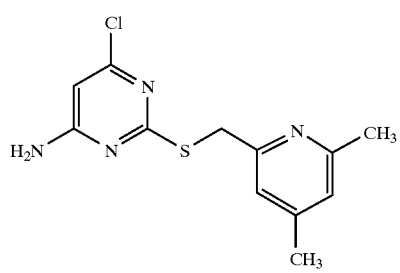
Cpd #122
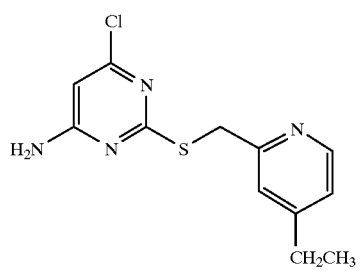
Cpd #123
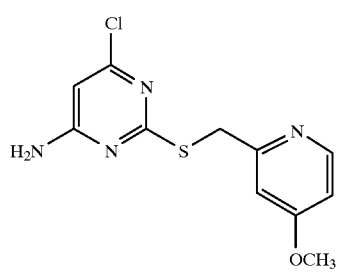
Cpd #124
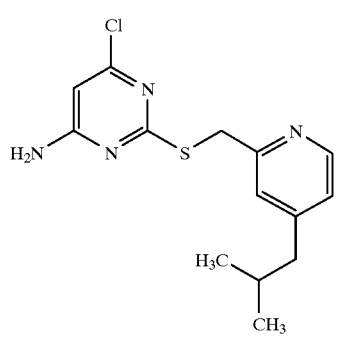
Cpd #125
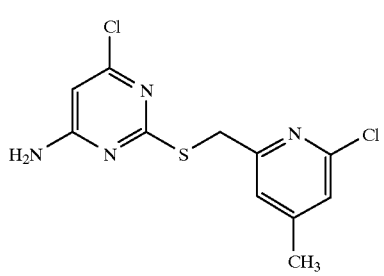
Cpd #126
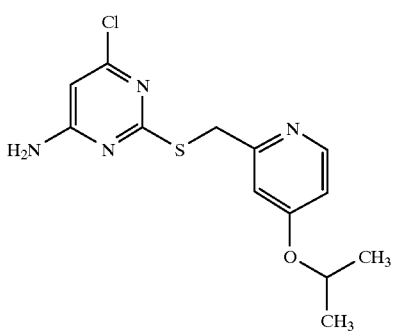
Cpd #127
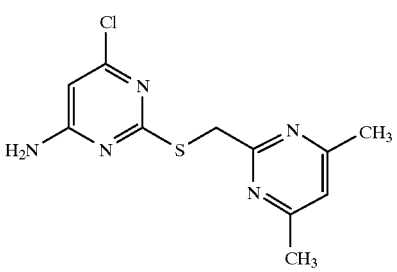
Cpd #128
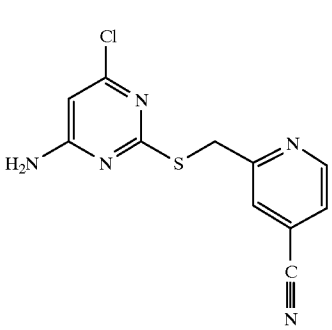
Cpd #130
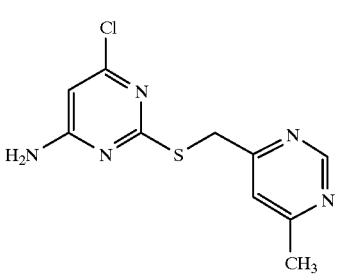
Cpd #131
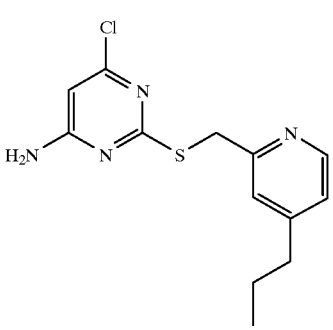

Cpd #132
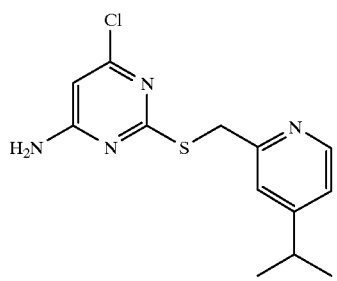
Cpd #133
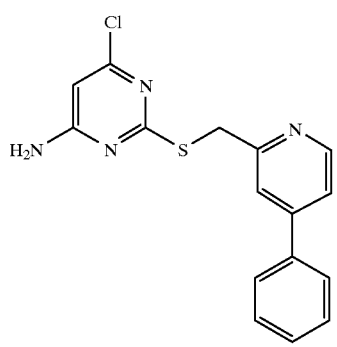
Cpd #134
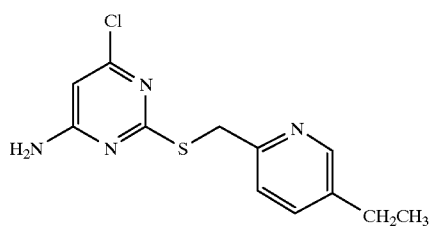
Cpd #135
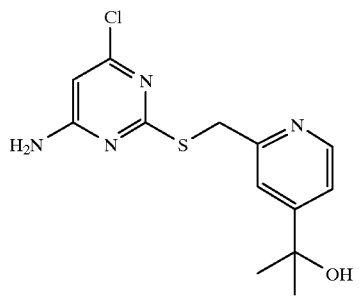
Cpd #137
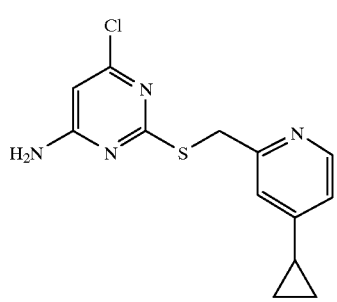
Cpd #138
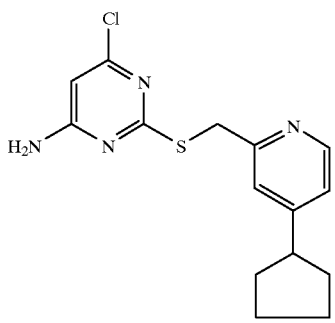
Cpd #140
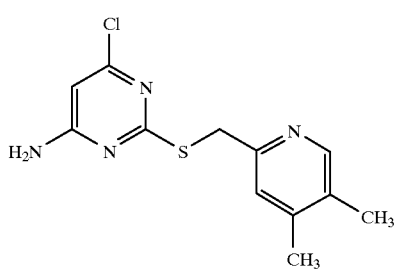
Cpd #142
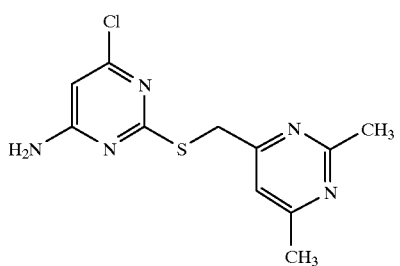
Cpd #143
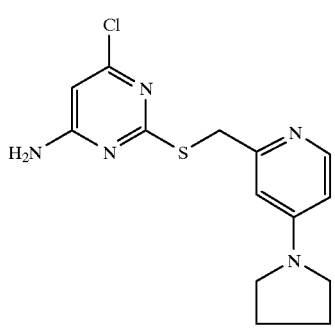
Cpd #144
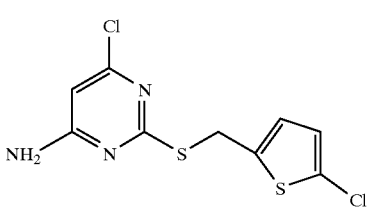

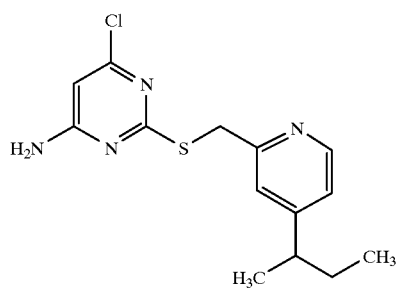
Cpd #145
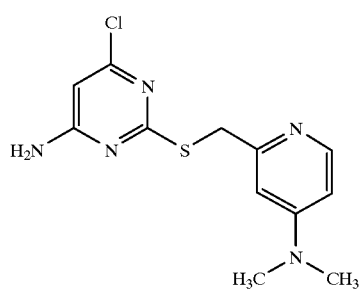
Cpd #146
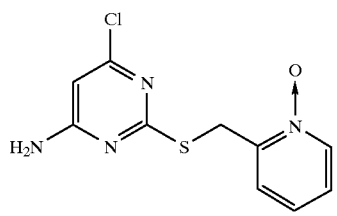
Cpd #147
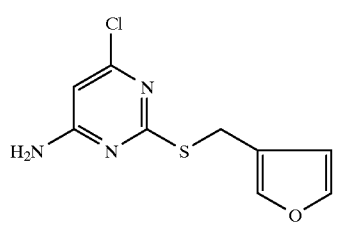
Cpd #148
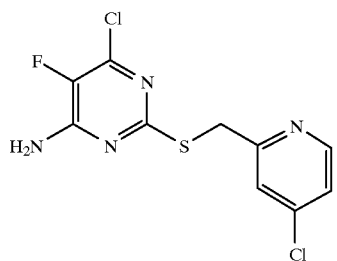
Cpd #149
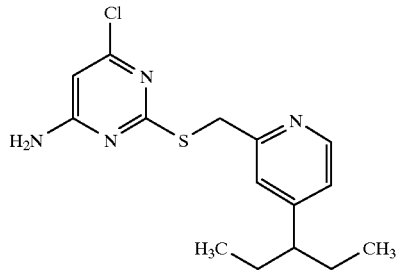
Cpd #151
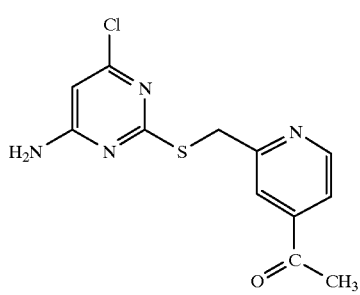
Cpd #152
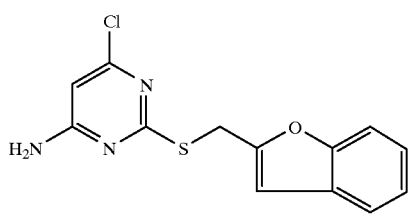
Cpd #153
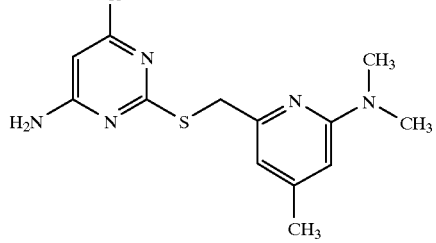
Cpd #154
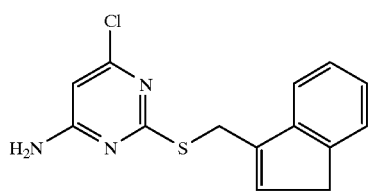
Cpd #155
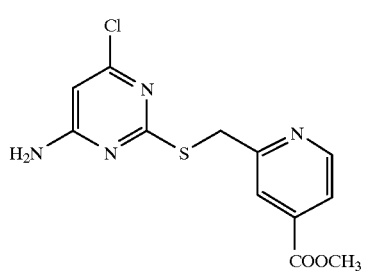
Cpd #156

Cpd #157
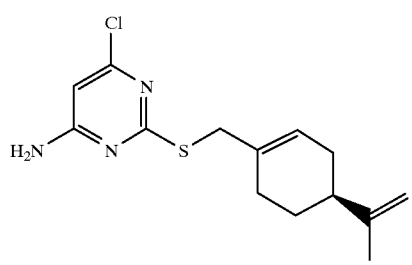
Cpd #165
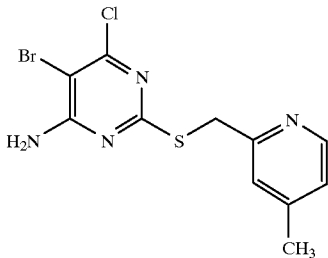
Cpd #158
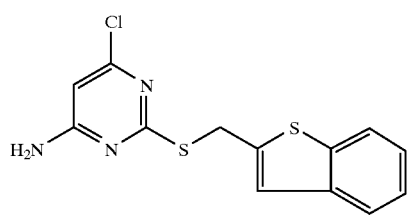
Cpd #166
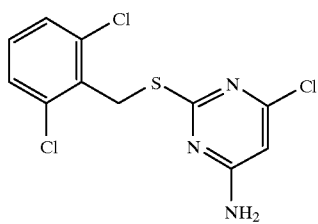
Cpd #159
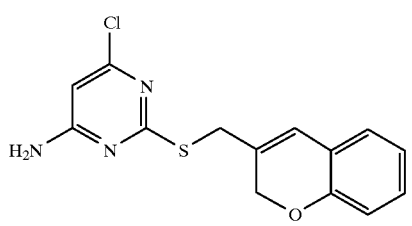
Cpd #167
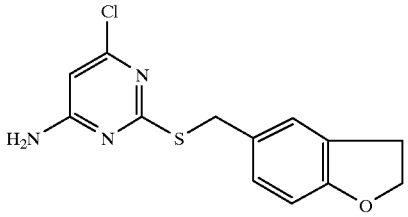
Cpd #163
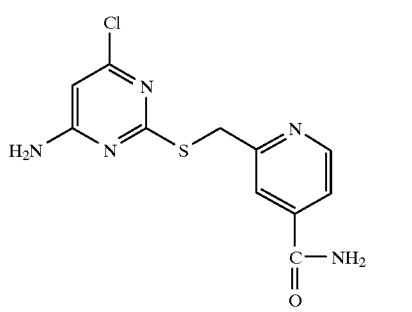
Cpd #168
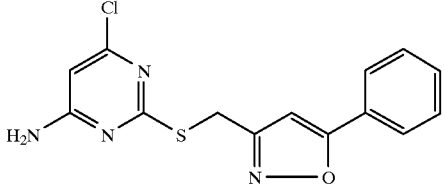
Cpd #164
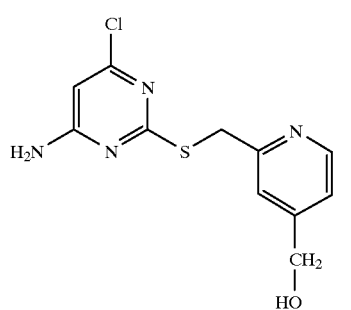
Cpd #169
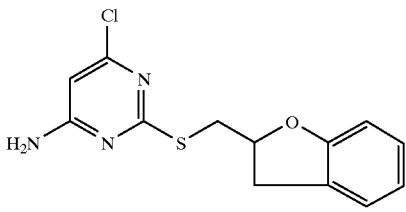
Cpd #170

Cpd #171
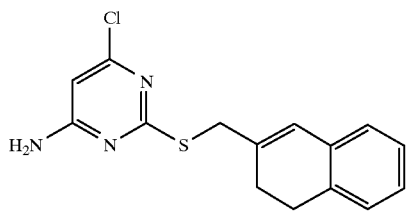
Cpd #172
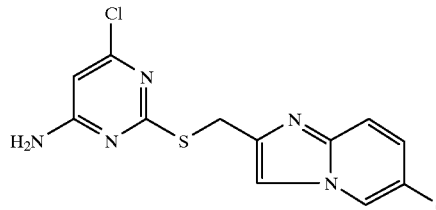
Cpd #173
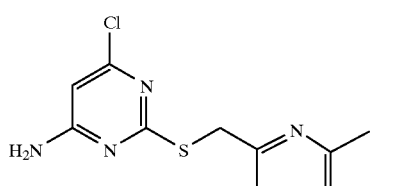
Cpd #174
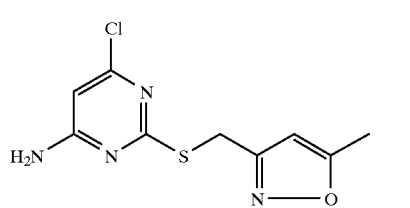
Cpd #175
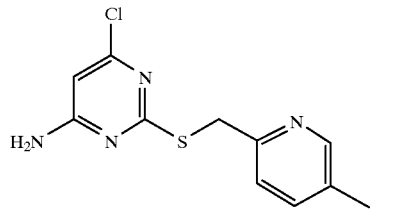
Cpd #176
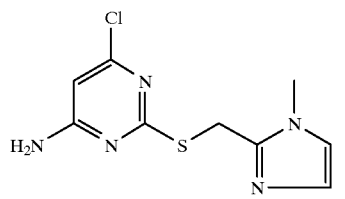
Cpd #177
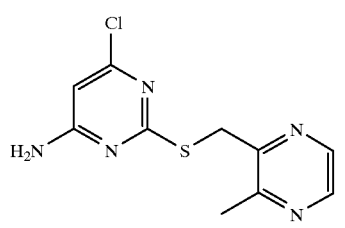
Cpd #178
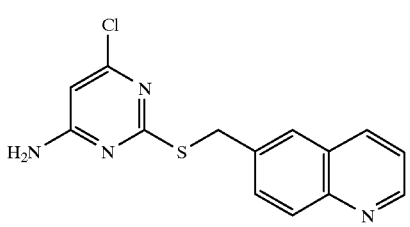
Cpd #179
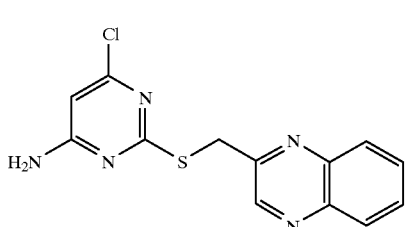
Cpd #180
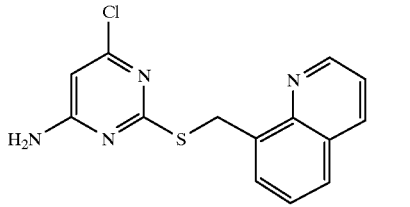
Cpd #181
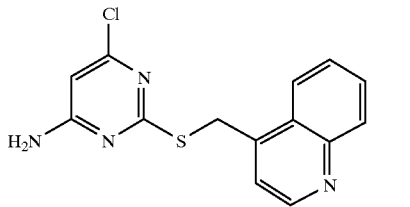
Cpd #182
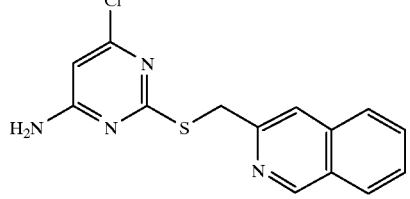
Cpd #183
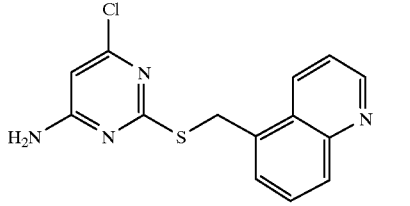

-continued
Cpd #184
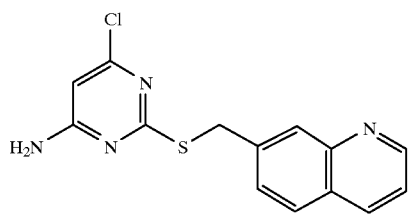
Cpd #186
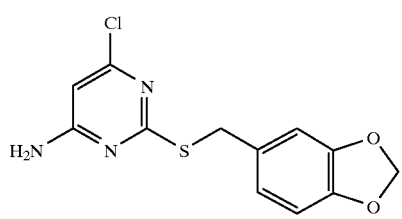
Cpd #187
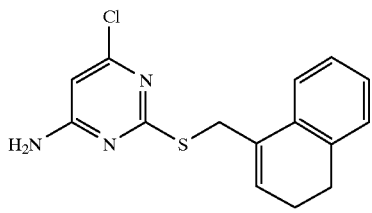
Cpd #188
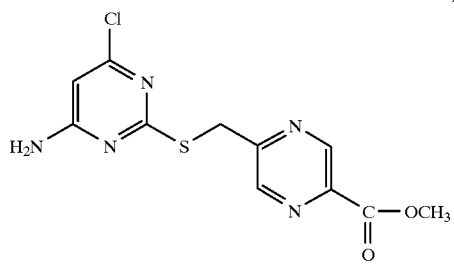
Cpd #189
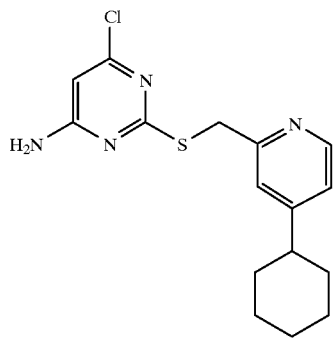
-continued
Cpd #190
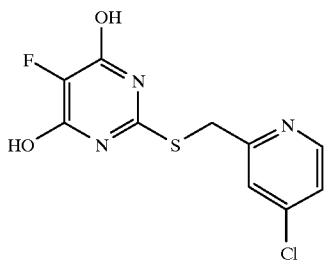
Cpd #191
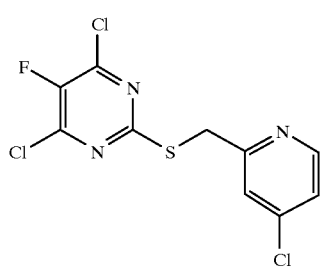
Cpd #192
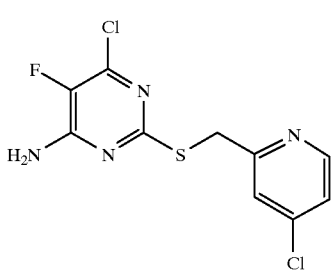
We claim:
1. A compound of Formula IA
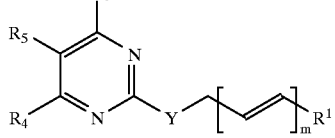
IA
where m is 0 or 1;
R$^1$ is selected from the group consisting —C≡CH,
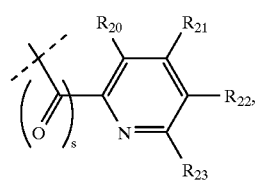
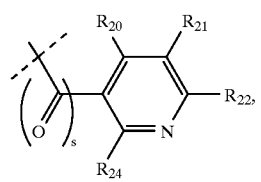

-continued

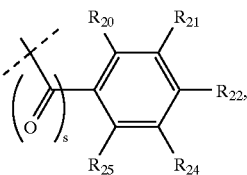

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, —halo, —OH, —CN, phenyl, phenylthio, —styryl, —$CO_2$($R_{31}$), —CON($R_{31}$)($R_{32}$), —CO($R_{31}$), —$(CH_2)_n$—N($R_{31}$)($R_{32}$), —C(OH)($R_{31}$)($R_{33}$), —$(CH_2)_n$N($R_{31}$)(CO($R_{33}$)), —$(CH_2)_n$N($R_{31}$)($SO_2$($R_{33}$)), or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2$OH, or —$(CH_2)_n$—N($R_{31}$)($R_{32}$) and the saturated ring may be optionally substituted with —H, $C_1$–$C_6$ alkyl, $C_1$–$C_6$ alkoxy, —OH, —$CH_2$OH, —$(CH_2)_n$—N($R_{31}$)($R_{32}$) or oxo (=O);

where n is 0–3 and $R_{31}$, $R_{32}$, and $R_{33}$ are the same or different and are selected from —H, $C_1$–$C_6$ alkyl, phenyl optionally substituted with 1, 2, or 3-halo, $C_1$–$C_6$ alkyl, $C_1$–$C_6$ alkoxy, —$CF_3$, —$NO_2$, —OH, —CN, or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl) piperazinyl;

or $R^1$ is a member selected from the group consisting of:
3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-2H-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3 c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3dihydro)-1H-indolyl, 6-(2,3-dihydro)-1H-indolyl, 7-(2,3-dihydro)-1H-indolyl, 4-(1,3dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl, 4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcylcohexen-1-yl or 4-dihydronaphth-2-yl;

and with the overall proviso that $R^1$ is not 2-pyrazinyl; and with the further proviso that $R^1$ is not 2- or 3-pyridinyl optionally substituted with $C_1$–$C_4$alkyl, a halogen atom, $NH_2$ or —OH;

$R_{20}$, $R_{21}$, $R_{22}$, $R_{23}$, $R_{24}$, $R_{25}$ are not $CO_2H$;

Y is selected from —S—, —S(O)—, —S(O)$_2$, or —O—;

$R_4$ is selected from the group consisting of —H or —$NR_{15}R_{16}$ where $R_{15}$ is —H and $R_{16}$ is —H, —$NH_2$ or $R_{15}$ and $R_{16}$ taken together with the —N form 1-pyrrolidino, 1-morpholino or 1-piperidino;

$R_5$ is selected from the group consisting of —H, halo, cyclohexyl, $C_1$–$C_4$ alkyl or $C_1$–$C_3$ alkoxy; and $R_6$ is selected from the group consisting of —H or halo, with the overall proviso that $R_4$ and $R_6$ are not both —H;

pharmaceutically acceptable salt, hydrate and n-oxide thereof; other than 2-benzylthio-4-morpholinopyrimidine, 4-amino-6-chloro-2-(benzylthio)-pyrimidine, 4-chloro-2-[(phenylmethyl)thio]-pyrimidine, 4-chloro-5-methoxy-2-[(phenylmethyl)thio]-pyrimidine, 4-chloro-5-bromo-2-[(phenylmethyl)thio]-pyrimidine, 4-chloro-5-methyl-2-[(phenylmethyl)thio]-pyrimidine, 4-chloro-5-methyl-2-[[(2,4-dichloro-phenyl)methyl]thio]-pyrimidine, 4-chloro-5-methyl-2-[[(2-chloro-phenyl)methyl]thio]-pyrimidine, 4-chloro-5-methyl-2-[[(4-chloro-phenyl)methyl]thio]-pyrimidine, 4-chloro-5-bromo-2-[[(4-chloro-phenyl)methyl]thio]-pyrimidine, 4-chloro-5-bromo-2-[[(2,4-dichloro-phenyl)methyl]thio]-pyrimidine, 4-chloro-5-bromo-2-[[(2-chloro-phenyl)methyl]thio]-pyrimidine, 2-[(phenylmethyl)thio]4-pyrimidinamine, 4-chloro-5-methoxy-2-(propargylthio)-pyrimidine, 4-amino-6-fluoro-2-(benzyloxy)-pyrimidine, 2-[[(4chlorophenyl)methyl]thio]-4-pyrimidinamine and 2-(phenylmethyoxy)-4-pyrimidinamine;

with the further proviso that when Y is S and m is 0, $R^1$ is other than substituted phenyl where $R_{20}$ is —$C_1$–$C_6$alkyl, $R_{21}$, is —OH and $R_{22}$ is —$CO(R_{31})$ where $R_{31}$ is $C_1$–$C_6$alkyl; and with the further proviso that when Y is S and m is 0, $R_6$ is H and $R_4$ is 1-piperidino, then $R^1$ is other than benzyl optionally substituted with halogen.

2. A compound according to claim 1 where s is 0 and Y is selected from the group consisting of —S, —S(O)— or —S(O)$_2$—.

3. A compound according to claim 1 where Y is —S—, m is 0 and s is 0.

4. A compound according to claim 1 where $R^1$ is selected from

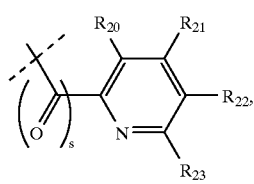

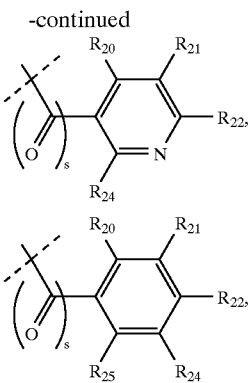

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, —halo, —OH, —CN, phenyl, phenylthio,-styryl, —$CO_2(R_{31})$, —$CON(R_{31})(R_{32})$, —$CO(R_{31})$, —$(CH_2)_n$—$N(R_{31})(R_{32})$, —$C(OH)(R_{31})(R_{33})$, —$(CH_2)_nN(R_{31})(CO(R_{33}))$, —$(CH_2)_nN(R_{31})(SO_2(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2OH$, or —$(CH_2)_n$—$N(R_{31})(R_{32})$ and the saturated ring may be optionally substituted with —H, $C_1$–$C_6$ alkyl, $C_1$–$C_6$ alkoxy, —OH, —$CH_2OH$, —$(CH_2)_n$—$N(R_{31})(R_{32})$ or oxo (=O);

where $R_{31}$, $R_{32}$, and $R_{33}$ are the same or different and are selected from —H, $C_1$–$C_6$ alkyl, phenyl optionally substituted with 1, 2, or 3-halo, $C_1$–$C_6$ alkyl, $C_1$–$C_6$ alkoxy, —$CF_3$, —$NO_2$, —OH, —CN, or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl.

5. A compound according to claim 1 wherein $R^1$ is selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3, 4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]

pyridinyl, 5-1H-pyrrolo[2,3-c]pyridinyl, 6-1H-pyrrolo [3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3, 2-c]pyridinyl, 4-(2,3-dihydro)-1H-pyrrolo[3,2-c] pyridinyl, 7-(2,3-dihydro)-1H-pyrrolo[2,3 c]pyridinyl, 6-(2,3-dihydro)-1H-pyrrolo [2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3, 4-b]pyridinyl, 6-1,7-naphthyridinyl, 6-2,7-naphthyridinyl, 7-2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3dihydro)-1H-indolyl, 6-(2,3-dihydro)-1H-indolyl, 7-(2,3-dihydro)-1H-indolyl, 4-(1,3dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl,4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran- 5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcylcohexen-1-yl or 4-dihydronaphth-2-yl.

6. A compound according to claim 1 where $R^1$ is phenyl optionally substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro;

$R_4$ is selected from the group consisting of —H or —NH$_2$; and $R_6$ is selected from the group consisting of —H or halo.

7. A compound according to claim 5 where s is 0 and Y is selected from the group consisting of —S—, —S(O)— or —S(O)$_2$—.

8. A compound according to claim 5 where s is 0 and Y is —S—.

9. A compound according to claim 1 and selected from the group consisting of:

4-amino-6-chloro-2-(3-methylphenylmethylthio)-pyrimidine (Cpd #36), 4-amino-6-chloro-2-(3-bromophenylmethylthio)-pyrimidine (Cpd #43), or 4-amino-6-chloro-2-(E-styrylmethylthio)-pyrimidine (Cpd #64), and pharmaceutically acceptable salts, hydrates and N-oxides thereof.

10. A method of treating an individual infected with the human immunodeficiency virus (HIV) which comprises administering an effective amount of an anti-AIDS compound of Formula IA

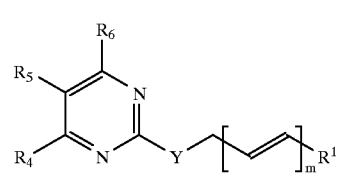

IA where m is 0 or 1;

$R^1$ is selected from the group consisting of —C≡CH,

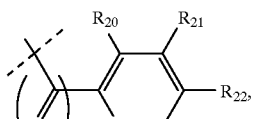

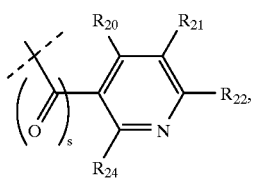

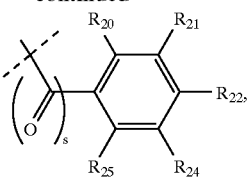

where s is 0 or 1 and $R_{20}$, $R_{21}$, $R_{22}$, $R_{23}$, $R_{24}$, and $R_{25}$ are the same or different and are selected from —H, $C_1$–$C_6$ alkyl, $C_1$–$C_6$ alkenyl, $C_1$–$C_6$ alkoxy, $C_1$–$C_6$ alkylthio, —$C_3$–$C_8$ cycloalkyl, —$CF_3$, —$NO_2$, —halo, —OH, —CN, phenyl, phenylthio, —styryl, —$CO_2(R_{31})$, —$CON(R_{31})(R_{32})$, —$CO(R_{31})$, —$(CH_2)_n$—$N(R_{31})(R_{32})$, —$C(OH)(R_{31})(R_{33})$, —$(CH_2)_nN(R_{31})(CO(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with —H, $C_1$–$C_6$ alkyl, $C_1$–$C_6$ alkoxy, —OH, —$CH_2OH$, or —$(CH_2)_n$—$N(R_{31})(R_{32})$ and the saturated ring may be optionally substituted with —H, $C_1$–$C_6$ alkyl, $C_1$–$C_6$ alkoxy, —OH, —$CH_2OH$, —$(CH_2)_n$— $N(R_{31})(R_{32})$ or oxo (=O);

where n is 0–3 and $R_{31}$, $R_{32}$, and $R_{33}$ are the same or different and are selected from —H, $C_1$–$C_6$ alkyl, phenyl optionally substituted with 1, 2, or 3-halo, $C_1$–$C_6$ alkyl, $C_1$–$C_6$ alkoxy, —$CF_3$, —$NO_2$, —OH, —CN, or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$–$C_6$alkyl)piperazinyl, or $R^1$ is a member selected from the group consisting of:

3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4dihydro)-2H-pyrano[2,3-c]pyridinyl, 6-(3,4-dihydro)-1H-pyrano[3,4c]pyridinyl, 7-(3,4-dihydro)-1H-pyrano[4,3-c]pyridinyl, 7-(3,4-dihydro)-2H-pyrano[3,2-c]pyridinyl, 5-(3,4dihydro)-2H-pyrano[3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b]pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo[3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3 c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b]pyridinyl, 6-1,7-naphthyridinyl, 6-2,7-naphthyridinyl, 7- 2,6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-(1,2,3,4-tetrahydro)-2,7-naphthyridinyl, 7-( 1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-( 1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2,3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3dihydro)-1H-indolyl, 6-(2,3-dihydro)-1H-indolyl, 7-(2,3-dihydro)-1H-indolyl, 4-(1,3dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H-1-benzopyranyl, 6-(3,4-dihydro)-2H-1-benzopyranyl, 7-3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3,4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl,4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S4-isopropenylcylcohexen-1-yl or 4-dihydronaphth-2-yl; and with the overall proviso that $R^1$ is not 2-pyrazinyl;

$R_{20}$, $R_{21}$, $R_{22}$, $R_{23}$, $R_{24}$, $R_{25}$ are not $CO_2H$;

Y is selected from —S—, —S(O)—, —S(O)$_2$, or —O—;

$R_4$ is selected from the group consisting of —H or —NR$_{15}$R$_{16}$ where $R_{15}$ is —H and $R_{16}$ is —H, $C_1$–$C_6$ alkyl, —NH$_2$ or $R_{15}$ and $R_{16}$ taken together with the —N form 1-pyrrolidino, 1-morpholino or 1-piperidino;

$R_5$ is selected from the group consisting of —H, halo, cyclohexyl, $C_1$–$C_4$ alkyl or $C_1$–$C_3$ alkoxy; and $R_6$ is selected from the group consisting of —H or halo, with the overall proviso that $R_4$ and $R_6$ are not both —H; and pharmaceutically acceptable salts and hydrates thereof.

11. A method according to claim 10 where s is 0 and Y is selected from the group consisting of —S—, —S(O)— or —S(O)$_2$—.

12. A method according to claim 10 where s is 0 and Y is —S—.

13. A method according to claim 10 where $R^1$ is is selected from a 3-isoquinolinyl, 1-isoquinolinyl, 2-quinolinyl, 3-quinolinyl, 3-(5,6,7,8-tetrahydro)-isoquinolinyl, 1-(5,6,7,8-tetrahydro)-isoquinolinyl, 2-(5,6,7,8-tetrahydro)-quinolinyl, 3-(5,6,7,8-tetrahydro)-quinolinyl, 3-(5,6-dihydro)-2H-2-pyridinyl, 1-(5,6-dihydro)-2H-2-pyridinyl, 2-(5,6-dihydro)-1H-1-pyridinyl, 3-(5,6-dihydro)-1H-1-pyridinyl, 5-furo[2,3-c]pyridinyl, 6-furo[3,2-c]pyridinyl, 4-furo[3,2-c]pyridinyl, 7-furo[2,3-c]pyridinyl, 6-furo[2,3-b]pyridinyl, 5-furo[3,2-b]pyridinyl, 5-(2,3-dihydro)-furo[2,3-c]pyridinyl, 6-(2,3-dihydro)-furo[3,2-c]pyridinyl, 4-(2,3-dihydro)-furo[3,2-c]pyridinyl, 7-(2,3-dihydro)-furo[2,3-c]pyridinyl, 6-(2,3-dihydro)-furo[2,3-b]pyridinyl, 5-(2,3-dihydro)-furo[3,2-b]pyridinyl, 6-(1,3-dihydro)-furo[3,4-c]pyridinyl, 4-(1,3-dihydro)-furo[3,4-c]pyridinyl, 2-(5,7-dihydro)-furo[3,4-b]pyridinyl, 6-(3,4-dihydro)-2H-pyrano[2,3-c]pyridinyl, 6-(3,4-dihydro)-1H-pyrano[3,4-c]pyridinyl, 7-(3,4-dihydro)-1H-pyrano[4,3-c]pyridinyl, 7-(3,4-dihydro)-2H-pyrano[3,2-c]pyridinyl, 5-(3,4-dihydro)-2H-pyrano [3,2-c]pyridinyl, 5-(3,4-dihydro)-1H-pyrano[4,3-c]pyridinyl, 8-(3,4-dihydro)-1H-pyrano[3,4-c]pyridinyl, 8-(3,4-dihydro)-2H-pyrano[2,3-c]pyridinyl, 7-(3,4-dihydro)-2H-pyrano[2,3-b]pyridinyl, 2-(5,6-dihydro)-1H-pyrano[3,4-b]pyridinyl, 2-(5,6-dihydro)-2H-pyrano[4,3-b]pyridinyl, 6-(3,4-dihydro)-2H-pyrano[3,2-b] pyridinyl, 5-1H-pyrrolo[2,3-c]pyridinyl, 6-1H-pyrrolo[3,2-c]pyridinyl, 4-1H-pyrrolo[3,2-c]pyridinyl, 7-1H-pyrrolo[2,3-c]pyridinyl, 6-1H-pyrrolo[2,3-b]pyridinyl, 5-1H-pyrrolo [3,2-b]pyridinyl, 5-(2,3-dihydro)-1H-pyrrolo[2,3-c]pyridinyl, 6-(2,3-dihydro)-1H-pyrrolo[3,2-c]pyridinyl, 4-(2,3-dihydro)-1H-pyrrolo[3,2-c]pyridinyl, 7-(2,3-dihydro)-1H-pyrrolo[2,3 c]pyridinyl, 6-(2,3-dihydro)-1H-pyrrolo[2,3-b]pyridinyl, 5-(2,3-dihydro)-1H-pyrrolo[3,2-b]pyridinyl, 6-(1,3-dihydro)-1H-pyrrolo[3,4-c]pyridinyl, 4-(1,3-dihydro)-1H-pyrrolo[3,4-c]pyridinyl, 2-(5,7-dihydro)-1H-pyrrolo[3,4-b] pyridinyl, 6-1,7-naphthyridinyl, 6-2,7-naphthyridinyl, 7-2, 6-naphthyridinyl, 7-1,6-naphthyridinyl, 5-1,6-naphthyridinyl, 5-2,6-naphthyridinyl, 8-2,7-naphthyridinyl, 8-1,7-naphthyridinyl, 7-1,8-naphthyridinyl, 2-1,7-naphthyridinyl, 2-1,6-naphthyridinyl, 6-1,5-naphthyridinyl, 6-(1,2,3,4-tetrahydro)-1,7-naphthyridinyl, 6-( 1,2,3,4-tetrahydro)-2,7-naphthyridinyl, 7-(1,2,3,4-tetrahydro)-2,6-naphthyridinyl, 7-(1,2,3,4-tetrahydro)-1,6-naphthyridinyl, 5-(1,2,3,4-tetrahydro)-1,6-naphthyridinyl, 5-(1,2,3,4-tetrahydro)-2,6-naphthyridinyl, 8-(1,2,3,4-tetrahydro)-2,7-naphthyridinyl, 8-(1,2,3,4-tetrahydro)-1,7-naphthyridinyl, 7-(1,2,3,4-tetrahydro)-1,8-naphthyridinyl, 2-(5,6,7,8-tetrahydro)-1,7-naphthyridinyl, 2-(5,6,7,8-tetrahydro)-1,6-naphthyridinyl, 6-(1,2,3,4-tetrahydro)-1,5-naphthyridinyl, 1-naphthyl, 2-naphthyl, 5-(1,2,3,4-tetrahydro)-naphthyl, 6-(1,2,3,4-tetrahydro)-naphthyl, 4-(2,3-dihydro)-1H-indenyl, 5-(2,3-dihydro)-1H-indenyl, 5-benzofuranyl, 4-benzofuranyl, 6-benzofuranyl, 7-benzofuranyl, 5-(2,3-dihydro)-benzofuranyl, 4-(2,3-dihydro)-benzofuranyl, 6-(2, 3-dihydro)-benzofuranyl, 7-(2,3-dihydro)-benzofuranyl, 4-(1,3-dihydro)-isobenzofuran, 5-(1,3-dihydro)-isobenzofuran, 4-1H-indolyl, 5-1H-indolyl, 6-1H-indolyl, 7-1H-indolyl, 4-(2,3-dihydro)-1H-indolyl, 5-(2,3dihydro)-1H-indolyl, 6-(2,3-dihydro)-1H-indolyl, 7-(2,3-dihydro)-1H-indolyl, 4-(1,3dihydro)-1H-isoindolyl, 5-(1,3-dihydro)-1H-isoindolyl, 5-(3,4-dihydro)-1H-2-benzopyranyl, 6-(3,4-dihydro)-1H-2-benzopyranyl, 7-(3,4-dihydro)-1H-2-benzopyranyl, 8-(3,4-dihydro)-1H-2-benzopyranyl, 5-(3,4-dihydro)-2H- 1-benzopyranyl, 6-(3,4-dihydro)-2H-1-benzopyranyl, 7-(3,4-dihydro)-2H-1-benzopyranyl, 8-(3,4-dihydro)-2H-1-benzopyranyl, 5-(1,2,3,4-tetrahydro)-isoquinolinyl, 6-(1,2,3,4-tetrahydro)-isoquinolinyl, 7-(1,2,3, 4-tetrahydro)-isoquinolinyl, 8-(1,2,3,4-tetrahydro)-isoquinolinyl, 5-(1,2,3,4-tetrahydro)-quinolinyl, 6-(1,2,3,4-tetrahydro)-quinolinyl, 7-(1,2,3,4-tetrahydro)-quinolinyl, 8-(1,2,3,4-tetrahydro)-quinolinyl,4-quinolinyl, 5-quinolinyl, 6-quinolinyl, 7-quinolinyl, 8-quinolinyl, 1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethyl-pyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcylcohexen-1-yl or 4-dihydronaphth-2-yl.

14. A method according to claim 10 where $R^1$ is phenyl optionally substituted with one, 2 or 3 $C_1$–$C_4$ alkyl, $C_1$–$C_8$ alkoxy, halo, $C_1$–$C_3$ alkylthio, trifluoromethyl, $C_2$–$C_6$ dialkylamino, or nitro.

15. A method according to claim 14 where s is 0.

16. A method according to claim 10 wherein $R^1$ is 2-pyridyl optionally substituted with —H, —$C_1$–$C_6$ alkyl, —$C_1$–$C_6$ alkoxy, —OH, —CH$_2$OH, —(CH$_2$)$_n$—N (R$_{31}$)(R$_{32}$).

17. A method according to claim 10 wherein $R^1$ is selected from 1-naphthyl or 2-naphthyl.

18. A method of treating an individual infected with the human immunodeficiency virus (HIV) according to claim 10 where the (1) infected individual is asymptomatic but tests positive for the HIV antigen, (2) infected individual is symptomatically sick but does not have "full blown AIDS", (3) individual infected with the human immunodeficiency virus (HIV) has "full blown AIDS".

19. A method of treating an individual infected with the human immunodeficiency virus (HIV) according to claim 10 where the administration is oral and the effective dose is from about 0.10 mg/kg/day to about 500 mg/kg/day.

20. A method of treating an individual infected with the human immunodeficiency virus (HIV) according to claim 10 where the compound is selected from the group consisting of 4-amino-6-chloro-2-(3-methylphenylmethylthio)-pyrimidine (Cpd #36), 4-amino-6-chloro-2-(3-bromophenylmethylthio)-
pyrimidine (Cpd #43), 4-amino-6-chloro-2-(E-styrylmethylthio)-pyrimidine
(Cpd #64), 4-amino-6-chloro-2-[2-(4-methyl)pyridylmethylthio]-
pyrimidine (Cpd #114), or 4-amino-6-chloro-2-[2-(4-isopropyl)-pyridylmethylthio]-
pyrimidine (Cpd #132), and pharmaceutically acceptable salts and hydrates thereof.

* * * * *